United States Patent
Sharma

(10) Patent No.: US 12,409,205 B2
(45) Date of Patent: Sep. 9, 2025

(54) NANOMOLECULES FOR THE TREATMENT OF INFLAMMATORY BOWEL DISEASES

(71) Applicant: Northwestern University, Evanston, IL (US)

(72) Inventor: Arun Sharma, Elmwood Park, IL (US)

(73) Assignee: Northwestern University, Evanston, IL (US)

( * ) Notice: Subject to any disclaimer, the term of this patent is extended or adjusted under 35 U.S.C. 154(b) by 894 days.

(21) Appl. No.: 17/047,299

(22) PCT Filed: Apr. 12, 2019

(86) PCT No.: PCT/US2019/027291
§ 371 (c)(1),
(2) Date: Oct. 13, 2020

(87) PCT Pub. No.: WO2019/200298
PCT Pub. Date: Oct. 17, 2019

(65) Prior Publication Data
US 2021/0113650 A1     Apr. 22, 2021

Related U.S. Application Data

(60) Provisional application No. 62/657,361, filed on Apr. 13, 2018.

(51) Int. Cl.
| | | |
|---|---|---|
| *A61K 38/10* | (2006.01) |
| *A61B 1/015* | (2006.01) |
| *A61B 1/31* | (2006.01) |
| *A61K 38/08* | (2019.01) |
| *A61K 47/54* | (2017.01) |
| *A61K 47/64* | (2017.01) |
| *A61K 49/00* | (2006.01) |
| *A61M 5/178* | (2006.01) |
| *A61P 1/00* | (2006.01) |
| *A61P 29/00* | (2006.01) |

(52) U.S. Cl.
CPC .............. *A61K 38/10* (2013.01); *A61B 1/015* (2013.01); *A61B 1/31* (2013.01); *A61K 38/08* (2013.01); *A61K 47/545* (2017.08); *A61K 47/64* (2017.08); *A61K 47/641* (2017.08); *A61K 49/0056* (2013.01); *A61M 5/178* (2013.01); *A61P 1/00* (2018.01); *A61P 29/00* (2018.01); *A61M 2210/1057* (2013.01); *A61M 2210/106* (2013.01); *A61M 2210/1064* (2013.01)

(58) Field of Classification Search
CPC ........ A61K 38/10; A61K 38/08; A61K 47/64; A61K 47/641; A61K 49/0056; A61B 1/015; A61B 1/31; A61M 5/178; A61M 2210/1057; A61M 2210/106; A61M 2210/1064; A61P 1/00; A61P 29/00
See application file for complete search history.

(56) References Cited

U.S. PATENT DOCUMENTS

| | | | |
|---|---|---|---|
| 6,890,654 B2 | 5/2005 | Stupp et al. | |
| 7,371,719 B2 | 5/2008 | Stupp et al. | |
| 7,390,526 B2 | 6/2008 | Stupp et al. | |
| 7,452,679 B2 | 11/2008 | Stupp et al. | |
| 7,491,690 B2 | 2/2009 | Stupp et al. | |
| 7,534,761 B1 | 5/2009 | Stupp et al. | |
| 7,544,661 B2 | 6/2009 | Stupp et al. | |
| 7,554,021 B2 | 6/2009 | Stupp et al. | |
| 7,683,025 B2 | 3/2010 | Stupp et al. | |
| 7,745,708 B2 | 6/2010 | Stupp et al. | |
| 7,838,491 B2 | 11/2010 | Stupp et al. | |
| 7,851,445 B2 | 12/2010 | Stupp et al. | |
| 8,063,014 B2 | 11/2011 | Stupp et al. | |
| 8,080,262 B2 | 12/2011 | Lee et al. | |
| 8,114,834 B2 | 2/2012 | Hsu et al. | |
| 8,114,835 B2 | 2/2012 | Mata et al. | |
| 8,124,583 B2 | 2/2012 | Stupp et al. | |
| 8,138,140 B2 | 3/2012 | Stupp et al. | |
| 8,450,271 B2 | 5/2013 | Shah et al. | |
| 8,512,693 B2 | 8/2013 | Capito et al. | |
| 11,161,876 B2 * | 11/2021 | Sharma | .................. C07K 7/08 |
| 2012/0021020 A1 | 1/2012 | Tomich et al. | |
| 2015/0218252 A1 | 8/2015 | Ingber et al. | |
| 2017/0051016 A1 | 2/2017 | Sharma | |

OTHER PUBLICATIONS

International Search Report and Written Opinion for PCT/US19/27291. Mailed Sep. 11, 2019. 16 pages.
Bury et al., Anti-Inflammatory Supramolecular Nanofibers to Modulate Inflammation in a Mouse Model of Illeitis, Gastroenterology, Apr. 2017, vol. 152, No. 5, Supplement 1 p. s570.
Evans. The Rise of Azide—Alkyne 1,3-Dipolar 'Click' Cycloaddition and its Application to Polymer Science and Surface Modification. Australian Journal of Chemistry (2007) 60: 384-395.
Israelachvili Intermolecular and surface forces; 2nd ed.; Academic: London San Diego, 1992.
Kolb et al., Click Chemistry: Diverse Chemical Function from a Few Good Reactions. Angew Chem Int Ed Engl. Jun. 1, 2001;40(11):2004-2021.
Mayo et al. Protein Science (1996), 5:1301-1315.
Tornoe et al., Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.

(Continued)

*Primary Examiner* — Robert S Cabral

(74) *Attorney, Agent, or Firm* — David W. Staple; Casimir Jones, S.C.

(57) ABSTRACT

Provided herein are anti-inflammatory peptide amphiphiles (AIF-PAs) and methods of use thereof. In particular, nanofiber of AIF-PAs are provided and methods of use thereof in the treatment of inflammatory bowel diseases (e.g., Crohn's disease).

19 Claims, 9 Drawing Sheets

Specification includes a Sequence Listing.

(56) References Cited

OTHER PUBLICATIONS

Viney et al., Mucosal addressin cell adhesion molecule-1: a structural and functional analysis demarcates the integrin binding motif. The Journal of Immunology, Sep. 15, 1996, vol. 157, No. 6, pp. 2488-2497, especially abstract, p. 2488, 2493.

* cited by examiner

NANOMOLECULES FOR THE TREATMENT OF INFLAMMATORY BOWEL DISEASES

FIELD

Provided herein are anti-inflammatory peptide amphiphiles (AIF-PAs) and methods of use thereof. In particular, nanofiber of AIF-PAs are provided and methods of use thereof in the treatment of inflammatory bowel diseases (e.g., Crohn's disease).

BACKGROUND

Patients suffering from inflammatory bowel disease (IBD) experience varying degrees of abdominal discomfort throughout their digestive tract. This may be caused by pathogenic infiltration, immune problems, or genetic causes that result in varying medical conditions. IBD affects approximately 1.6 million patients in the United States of which 80,000 of those are children. This results in a staggering direct cost for patient related issues that ranges from $11-28 billion annually. However, a specific form of IBD, namely Crohn's Disease (CD), is more menacing and presents dire consequences even if timely medical intervention is initiated. CD affects a wide swath of ethnicities but is more common in Caucasian and African-American populations, less common in Latino and Asian populations, and people of Ashkenazi descent are at 4-5 higher risk than the general population.

CD typically affects the entire length and circumference of the small intestine and the upper large intestine. The disease manifests itself in the form of patchy lesions that are sporadically located along the intestines and penetrate the full thickness of the tissue itself. At the onset of the disease, the intestinal tissue progresses through several stages of inflammation which becomes increasingly worse over time. In normal situations, the body uses the inflammatory response to combat a variety of foreign insults as well as participate in body homeostasis at multiple levels. However, when the inflammatory response becomes unmanageable by the body, due to a number of factors, severe tissue damage and/or tissue death occurs. Manifestations of the disease include continual abdominal pain, bleeding and tissue rupturing, nutrient malabsorption, poor overall body growth and development, repeated surgical procedures, and the potential of intestinal cancer. Quality of life issues relating to CD range from depression, negative body image issues and social stigmas, and the negative impact on professional and family lifestyles. These attributes further contribute to the overall deterioration of this patient population.

Treatment options available to CD patients range from prescribed oral medications to biological reagents specifically designed to combat the hyperactive inflammatory response. However, a large percentage of the CD population that responds poorly to these treatment options, if at all. Further problems with current treatment options are that they are quite expensive, are inefficient, and have numerous side effects including the potential of inducing different types of cancer. CD patients experience recurrent flare-ups and typically require a highly invasive surgery to remove the dying or dead tissue. It is estimated that 70% of those with CD will require surgery over their lifetime and 30% and 60% of those will require additional surgery at 3 and 10 years post-initial surgery, respectively. There still exists an unmet clinical need to address the issues surrounding the highly pro-inflammatory local environment in CD patients.

SUMMARY

Provided herein are anti-inflammatory peptide amphiphiles (AIF-PAs) and methods of use thereof. In particular, nanofiber of AIF-PAs are provided and methods of use thereof in the treatment of inflammatory bowel diseases (e.g., Crohn's disease).

In some embodiments, provided herein are compositions (e.g., pharmaceutical compositions) comprising peptide amphiphiles comprising (a) a nanofiber-forming moiety, and (b) an anti-inflammatory (AIF) peptide. In some embodiments, the nanofiber-forming moiety comprises hydrophobic segment, structural segment, and a charged segment, wherein the nanofiber-forming moiety self-assembles under aqueous conditions with other similar nanofiber-forming moieties to form a peptide amphiphile nanofiber. In some embodiments, the hydrophobic segment is a carbon chain of 8-20 (e.g., 8, 9, 10, 11, 12, 13, 14, 15, 16, 17, 18, 19, 20, or ranges therebetween) carbons in length. In some embodiments, the structural segment is a β-sheet forming segment. In some embodiments, the structural segment comprises VVVAAA (SEQ ID NO: 6) or VVAA (SEQ ID NO: 7). In some embodiments, the charged segment is an acidic segment comprising a plurality of E and/or D residues. In some embodiments, the acidic segment comprises EE. In some embodiments, the charged segment is a basic segment comprising a plurality of H, K and/or R residues. In some embodiments, the nanofiber-forming moiety comprises $C_{16}$-VVVAAAEEE (SEQ ID NO: 9). In some embodiments, the AIF peptide comprises MQMKKVLDS (SEQ ID NO: 1), HDMNKVLDL (SEQ ID NO: 2), KVLDPVKG (SEQ ID NO:3), KVLDGQDP (SEQ ID NO: 4), DPVKG (SEQ ID NO: 5), peptides comprising only conservative or semi-conservative substitutions with respect to one or SEQ ID NOs 1-5, or peptides comprising at least 70% (e.g., 70%, 75%, 80%, 85%, 90%, 95%, or ranges therebetween) sequence identity with one of SEQ ID NOs 1-5. In some embodiments, the AIF peptide comprises KVLDS (SEQ ID NO: 8). In some embodiments, the nanofiber-forming moiety comprises $C_{16}$-VVVAAAEEE (SEQ ID NO: 9) and the AIF peptide comprises KVLDS (SEQ ID NO: 8).

In some embodiments, provided herein are branched peptide amphiphiles comprising a nanofiber-forming moiety that displays an AIF peptide and one or more additional functional moieties. In some embodiments, the nanofiber-forming moiety comprises hydrophobic segment, structural segment, and a charged segment, wherein the nanofiber-forming moiety self-assembles under aqueous conditions with other similar nanofiber-forming moieties to form a peptide amphiphile nanofiber. In some embodiments, the hydrophobic segment is a carbon chain of 8-20 (e.g., 8, 9, 10, 11, 12, 13, 14, 15, 16, 17, 18, 19, 20, or ranges therebetween) carbons in length. In some embodiments, the structural segment is a β-sheet forming segment. In some embodiments, the structural segment comprises VVVAAA (SEQ ID NO: 6) or VVAA (SEQ ID NO: 7). In some embodiments, the charged segment is an acidic segment comprising a plurality of E and/or D residues. In some embodiments, the acidic segment comprises EE. In some embodiments, the charged segment is a basic segment comprising a plurality of H, K and/or R residues. In some embodiments, the nanofiber-forming moiety comprises $C_{16}$-VVVAAAEEE (SEQ ID NO: 9). In some embodiments, the AIF peptide comprises MQMKKVLDS (SEQ ID NO: 1), HDMNKVLDL (SEQ ID NO: 2), KVLDPVKG (SEQ ID NO: 3), KVLDGQDP (SEQ ID NO: 4), DPVKG (SEQ ID NO: 5), peptides comprising only conservative or semi-conservative substitutions with respect to one or SEQ ID NOs 1-5, or peptides comprising at least 70% (e.g., 70%, 75%, 80%, 85%, 90%, 95%, or ranges therebetween) sequence identity with one of SEQ ID NOs 1-5. In some embodiments, the AIF peptide comprises KVLDS (SEQ ID NO: 8). In some embodiments, the nanofiber-forming moiety comprises $C_{16}$-VVVAAAEEE (SEQ ID NO: 9) and the AIF peptide comprises KVLDS (SEQ ID NO: 8). In some embodiments, the one or more additional functional moieties comprises a targeting moiety. In some embodiments, the targeting moiety is a targeting peptide. In some embodiments, the targeting peptide comprises LDT. In some embodiments, the one or more additional functional moieties comprises a visualization moiety. In some embodiments, the visualization moiety is a small molecule fluorophore. In some embodiments, the visualization moiety comprises TAMRA. In some embodiments, the one or more additional functional moieties comprises a targeting moiety and a visualization moiety. In some embodiments, the peptide amphiphile is branched at one or more lysine residues.

In some embodiments, provided herein are methods of treating an inflammatory condition comprising administering a peptide amphiphile composition described herein to a subject. In some embodiments, the composition is administered systemically to the subject. In some embodiments, the composition is administered locally to a site of inflammation. In some embodiments, the inflammatory condition comprises a bowel disease. In some embodiments, the composition is formulated as a suppository and is administered rectally. In some embodiments, the composition is formulated for topical administration and is administered by endoscope. In some embodiments, the composition is formulated for injection and is administered by endoscope.

In some embodiments, provided herein are nanofibers comprising the peptide amphiphile compositions described herein. In some embodiments, the nanofibers display the AIF peptide on their exterior. In some embodiments, the nanofibers display the one or more additional functional moieties (e.g., targeting peptide, fluorophore) on their exterior.

In some embodiments, provided herein are systems comprising: (a) a peptide amphiphile composition described herein; and (b) a medical device for administering the composition to a site of inflammation within the bowels of a subject. In some embodiments, the medical device is a syringe, catheter, or endoscope.

In some embodiments, provided herein is the use of the peptide amphiphile composition described herein for the treatment of an inflammatory condition. In some embodiments, the inflammatory condition comprises a bowel disease. In some embodiments, the bowel disease is Crohn's disease.

In some embodiments, provided herein are methods, compositions, and systems for the synthesis and/or assembly of branched peptide amphiphiles (e.g., using lysine residue(s) for branch points and/or click chemistry for attaching components).

DEFINITIONS

Figure 1:
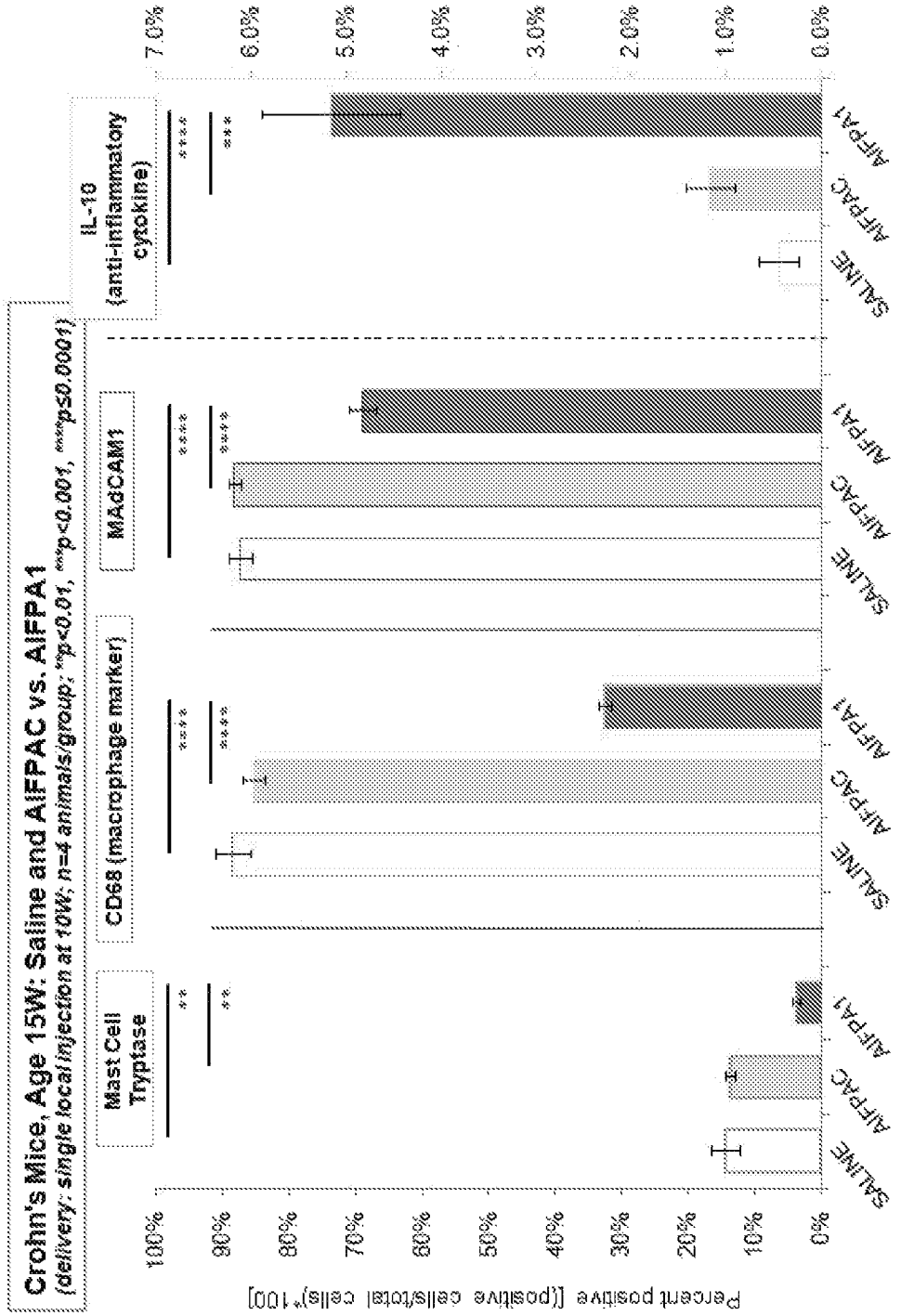
FIG. 1. Cell/marker expression following treatment of SAMP1/YitFcsJ mice (Crohn's mice). Following direct treatment injection of either saline, AIF-PAC or AIF-PA1 into inflamed intestinal lesions of SAMP1/YitFcsJ mice, the mice were evaluated for the expression of specific inflammatory cell epitopes [mast cell tryptase (mast cells); CD68 (macrophages)], a marker associated with ileitis based inflammation (MAdCAM1), and the anti-inflammatory cytokine interleukin-10 (IL-10). Data demonstrate a statistically significant decrease in pro-inflammatory mast cell tryptase, CD68, and MAdCAM1 with a concomitant increase in anti-inflammatory cytokine IL-10 in AIF-PA1 treated animals compared to AIF-PAC and saline injected control animals.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("Octan"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "artificial" refers to compositions and systems that are designed or prepared by man, and are not naturally occurring. For example, an artificial peptide, peptoid, or nucleic acid is one comprising a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO: Z (e.g., 100 amino acids) may have up to X substitutions (e.g., 10) relative to SEQ ID NO: Z, and may therefore also be expressed as "having X (e.g., 10) or fewer substitutions relative to SEQ ID NO: Z."

As used herein, the term "peptoid" refers to a class of peptidomimetics where the side chains are functionalized on the nitrogen atom of the peptide backbone rather than to the α-carbon.

As used herein, the term "nanofiber" refers to an elongated or threadlike filament (e.g., having a significantly greater length dimension that width or diameter) with a diameter typically less than 100 nanometers.

As used herein, the term "supramolecular" (e.g., "supramolecular complex," "supramolecular interactions," "supramolecular fiber," "supramolecular polymer," etc.) refers to the non-covalent interactions between molecules (e.g., polymers, marcomolecules, etc.) and the multicomponent assemblies, complexes, systems, and/or fibers that form as a result.

As used herein, the term "physiological conditions" refers to the range of conditions of temperature, pH and tonicity (or osmolality) normally encountered within tissues in the body of a living human.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "peptide amphiphile" refers to a molecule that, at a minimum, includes a non-peptide lipophilic (hydrophobic) segment, a structural peptide segment and optionally a functional peptide segment. The peptide amphiphile may express a net charge at physiological pH, either a net positive or negative net charge, or may be zwitterionic (i.e., carrying both positive and negative charges). Certain peptide amphiphiles consist of or comprise: (1) a hydrophobic, non-peptidic segment (e.g., comprising an acyl group of six or more carbons), (2) a β-sheet-forming peptide segment; (3) a carboxyl-rich peptide segment, and (4) a functional moiety.

As used herein and in the appended claims, the term "lipophilic moiety" or "hydrophobic moiety" refers to the moiety disposed on the N-terminus of the peptide amphiphile (e.g., an acyl moiety), and may be herein and elsewhere referred to as the lipophilic or hydrophobic segment or component. The hydrophobic component should be of a sufficient length to provide amphiphilic behavior and micelle (or nanosphere or nanofiber) formation in water or another polar solvent system.

Accordingly, in the context of the embodiments described herein, the hydrophobic component preferably comprises a single, linear acyl chain of the formula: $C_{n-1}H_{2n-1}C(O)$— where n=6-22. In some embodiments, a linear acyl chain is the lipophilic group, palmitic acid. However, other small lipophilic groups may be used in place of the acyl chain. As used herein, the term "structural peptide" refers to a portion of a peptide amphiphile, typically disposed between the hydrophobic segment and the charged peptide segment. The structural peptide is generally composed of three to ten amino acid residues with non-polar, uncharged side chains (e.g., His (H), Val (V), Ile (I), Leu (L), Ala (A), Phe (F)) selected for their propensity to form hydrogen bonds or other stabilizing interactions (e.g., hydrophobic interactions, van der Waals' interactions, etc.) with structural segments of adjacent structural segments. In some embodiments, nanofibers of peptide amphiphiles having structural peptide segments display linear or 2D structure when examined by microscopy and/or α-helix and/or β-sheet character when examined by circular dichroism (CD).

As used herein, the term "beta (β)-sheet-forming peptide segment" refers to a structural peptide segment that has a propensity to display β-sheet-like character (e.g., when analyzed by CD). In some embodiments, amino acids in a beta (β)-sheet-forming peptide segment are selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety).

As used herein, the term "charged peptide segment" refers to a portion of a peptide amphiphile that is rich (e.g., >50%, >75%, etc.) in charged amino acid residues, or amino acid residue that have a net positive or negative charge under physiologic conditions. A charged peptide segment may be acidic (e.g., negatively charged), basic (e.g., positively charged), or zwitterionic (e.g., having both acidic and basic residues).

As used herein, the terms "carboxy-rich peptide segment," "acidic peptide segment," and "negatively-charged peptide segment" refer to a peptide sequence of a peptide amphiphile that comprises one or more amino acid residues that have side chains displaying carboxylic acid side chains (e.g., Glu (E), Asp (D), or non-natural amino acids). A carboxy-rich peptide segment may optionally contain one or more additional (e.g., non-acidic) amino acid residues. Non-natural amino acid residues, or peptidomimetics with acidic side chains could be used, as will be evident to one ordinarily skilled in the art. There may be from about 2 to about 7 amino acids, and or about 3 or 4 amino acids in this segment.

As used herein, the terms "amino-rich peptide segment", "basic peptide segment," and "positively-charged peptide segment" refer to a peptide sequence of a peptide amphiphile that comprises one or more amino acid residues that have side chains displaying positively-charged acid side chains (e.g., Arg (R), Lys (K), His (H), or non-natural amino acids, or peptidomimetics). A basic peptide segment may optionally contain one or more additional (e.g., non-basic) amino acid residues. Non-natural amino acid residues with basic side chains could be used, as will be evident to one ordinarily skilled in the art. There may be from about 2 to about 7 amino acids, and or about 3 or 4 amino acids in this segment.

As used herein, the term "functional peptide" refers to amino acid sequences that mediate the action of sequences, molecules, or supramolecular complexes associated therewith (e.g., an anti-inflammatory peptide). Peptide amphiphiles and structures (e.g., nanofibers) bearing functional peptides (e.g., anti-inflammatory peptides, etc.) exhibits the functionality of the functional peptide.

As used herein, the term "percent sequence identity" refers to the degree (e.g., 50%, 60%, 70%, 80%, 90%, 95%, 98%, 99%, 100%, ranges therebetween, etc.) to which two polymer sequences (e.g., peptide, polypeptide, nucleic acid, etc.) have the same sequential composition of monomer subunits. If two polymers have identical sequences (e.g., 100% sequence identity) they may be referred to herein as having "sequence identity." The term "percent sequence similarity" refers to the degree (e.g., 50%, 60%, 70%, 80%, 90%, 95%, 98%, 99%, 100%, ranges therebetween, etc.) with which two polymer sequences (e.g., peptide, polypeptide, nucleic acid, etc.) have similar polymer sequences (e.g., only conservative substitutitions between the sequences). For example, similar amino acids are those that share the same biophysical characteristics and can be grouped into the families (see "conservative amino acid substitution" below). If two polymers have sequences that have monomers at each position that share the same biophysical characteristics they may be referred to herein as having "sequence similarity." The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

A "conservative" amino acid substitution refers to the substitution of an amino acid in a polypeptide with another amino acid having similar properties, such as size or charge. In certain embodiments, a polypeptide comprising a conservative amino acid substitution maintains at least one activity of the unsubstituted polypeptide. A conservative amino acid substitution may encompass non-naturally occurring amino acid residues, which are typically incorporated by chemical peptide synthesis rather than by synthesis in biological systems. These include, but are not limited to, peptidomimetics and other reversed or inverted forms of amino acid moieties. Naturally occurring residues may be divided into classes based on common side chain properties, for example: hydrophobic: norleucine, Met, Ala, Val, Leu, and Ile; neutral hydrophilic: Cys, Ser, Thr, Asn, and Gln; acidic:

Asp and Glu; basic: His, Lys, and Arg; residues that influence chain orientation: Gly and Pro; and aromatic: Trp, Tyr, and Phe. Non-conservative substitutions may involve the exchange of a member of one of these classes for a member from another class; whereas conservative substitutions may involve the exchange of a member of one of these classes for another member of that same class.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence "having at least Y % sequence identity with SEQ ID NO: Z" may have up to X substitutions relative to SEQ ID NO: Z, and may therefore also be expressed as "having X or fewer substitutions relative to SEQ ID NO: Z."

As used herein, the term "pharmaceutically acceptable carrier" refers to non-toxic solid, semisolid, or liquid filler, diluent, encapsulating material, formulation auxiliary, or carrier conventional in the art for use with a therapeutic agent for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. A "pharmaceutical composition" typically comprises at least one active agent and a pharmaceutically acceptable carrier.

As used herein, the term "effective amount" refers to the amount of a composition (e.g., pharmaceutical composition) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., pharmaceutical compositions herein) to a subject or in vivo, in vitro, or ex vivo cells, tissues, and organs. Exemplary routes of administration to the human body can be through the eyes (e.g., intraocularly, intravitrealy, periocularly, ophthalmic, etc.), mouth (oral), skin (transdermal), nose (nasal), lungs (inhalant), oral mucosa (buccal), ear, rectal, by injection (e.g., intravenously, subcutaneously, intratumorally, intraperitoneally, etc.) and the like.

As used herein, the terms "co-administration" and "co-administer" refer to the administration of at least two agent(s) or therapies to a subject. In some embodiments, the co-administration of two or more agents or therapies is concurrent (e.g., in the same or separate formulations). In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "bowels" refers to the portions of the alimentary canal below the stomach, including the small intestine (e.g., jejunum, duodenum, ileum) and large intestine (e.g., cecum, ascending colon, transverse colon, descending colon, sigmoid colon).

The term bowel diseases includes, for example, irritable bowel syndrome (IBS), uncontrolled diarrhea-associated Irritable Bowel Syndrome (dIBS), Crohn's disease, traveler's diarrhea, ulcerative colitis, enteritis, small intestinal bacterial overgrowth, chronic pancreatitis, pancreatic insufficiency, colitis, diverticular disease, fibromyalgia, systemic lupus erythematosus or hepatic encephalopathy.

As used herein, "click chemistry" refers to a chemical philosophy tailored to generate substances quickly and reliably by joining small units together (see, e.g., Kolb, Finn and Sharpless *Angewandte Chemie International Edition* (2001) 40: 2004-2021; Evans, *Australian Journal of Chemistry* (2007) 60: 384-395; herein incorporated by reference in their entireties). The reactions in Click chemistry are modular, wide in scope, give high chemical yields, generate inoffensive byproducts, are stereospecific, are physiologically stable, exhibit a large thermodynamic driving force, and/or have high atom economy. Several reactions have been identified which fit this concept: (1) The Huisgen 1,3-dipolar cycloaddition (e.g., the Cu(I)-catalyzed stepwise variant, often referred to simply as the "click reaction"; see, e.g., Tornoe et al., *Journal of Organic Chemistry* (2002) 67: 3057-3064). Copper and ruthenium are the commonly used catalysts in the reaction. The use of copper as a catalyst results in the formation of 1,4-regioisomer whereas ruthenium results in formation of the 1,5-regioisomer; (2) other cycloaddition reactions, such as the Diels-Alder reaction; (3) nucleophilic addition to small strained rings like epoxides and aziridines; (4) nucleophilic addition to activated carbonyl groups; and (4) addition reactions to carbon-carbon double or triple bonds.

DETAILED DESCRIPTION

Provided herein are anti-inflammatory peptide amphiphiles (AIF-PAs) and methods of use thereof. In particular, nanofiber of AIF-PAs are provided and methods of use thereof in the treatment of inflammatory bowel diseases (e.g., Crohn's disease).

Provided herein are peptide amphiphiles displaying anti-inflammatory peptides. Such peptide amphiphiles comprise a hydrophobic segment, a structural peptide, and a charged peptide linked (e.g., directly or via one or more linker segments or moieties) to an anti-inflammatory peptide. In some embodiments, peptide amphiphiles additionally comprise one or more other functional moieties (e.g., peptides, small molecules, etc.). In some embodiments, provided herein are branched peptide amphipiles comprising a peptide amphiphile (e.g., hydrophobic segment/structural peptide/charged peptide) displaying two or more functional moieties (e.g., peptides, small molecules, etc.). In some embodiments, provided herein are systems and methods for the synthesis of branched peptide amphiphiles (e.g., using click chemistry, using lysine residues as branch points, etc.), and the branched peptide amphiphiles produced thereby. In some embodiments, provided herein are branched peptide amphiphiles comprising a peptide amphiphile portion (e.g., hydrophobic segment/structural peptide/charged peptide) and displaying (i) an anti-inflammatory peptide and targeting peptide, (ii) an anti-inflammatory peptide and visualization moiety (e.g., fluorophore), or (iii) an anti-inflammatory peptide, targeting peptide, and visualization moiety (e.g., fluorophore). Although described in detail herein is the use of these systems and methods for use in the synthesis of inti-inflammatory peptide amphiphiles, they also find use in the synthesis of branched peptide amphiphiles displaying other functional moieties. The above embodiments are described in more detail below.

In some embodiments, the peptide amphiphile molecules and compositions of the embodiments described herein are synthesized using preparatory techniques well-known to those skilled in the art, preferably, by standard solid-phase peptide synthesis, with the addition of a fatty acid in place of a standard amino acid at the N-terminus of the peptide, in order to create the lipophilic segment. For example, synthesis typically starts from the C-terminus, to which amino acids are sequentially added using either a Rink amide resin (resulting in an —$NH_2$ group at the C-terminus of the peptide after cleavage from the resin), or a Wang resin (resulting in an —OH group at the C-terminus). Accordingly, embodiments described herein encompasses peptide amphiphiles having a C-terminal moiety that may be selected from the group consisting of —H, —OH, —COOH, —$CONH_2$, and —$NH_2$. The lipophilic or hydrophobic segment is typically incorporated at the N-terminus of the peptide after the last amino acid coupling, and is composed of a fatty acid or other acid that is linked to the N-terminal amino acid through an acyl bond (although the lipophilic or hydrophobic segment may be attached to the C-terminus). In aqueous solutions, PA molecules self-assemble (e.g., into cylindrical micelles (a.k.a nanofibers)) that bury the lipophilic segment in their core and display the functional peptide(s) (e.g., AIF) on the surface. In some embodiments, the structural peptide (e.g., VVVAAA) undergoes intermolecular hydrogen bonding to form beta sheets that orient parallel to the long axis of the micelle.

In some embodiments, PA molecules herein comprise a nanofiber-forming moiety that in turn comprises a hydrophobic segment and a peptide segment. In certain embodiments, a hydrophobic (e.g., hydrocarbon and/or alkyl tail) segment of sufficient length (e.g., >3 carbons, >5 carbons, >7 carbons, >9 carbons, >11, >13, >15, etc.) is covalently coupled to peptide segment (e.g., an ionic peptide having a preference for beta-strand conformations) to yield a peptide amphiphile molecule. In some embodiments, a plurality of such PAs will self-assemble in water (or aqueous solution) into a nanostrcuture (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; 2nd ed.; Academic: London San Diego, 1992; herein incorporated by reference in its entirety). Other molecular shapes have similar effects on assembly and nanostrcutural architecture. In various embodiments, hydrophobic segments pack in the center of the assembly with the peptide segments exposed to an aqueous or hydrophilic environment to form cylindrical nanostructures that resemble filaments. Such nanofilaments display the peptide regions on their exterior and have a hydrophobic core.

In some embodiments, to induce self-assembly of an aqueous solution of peptide amphiphiles, the pH of the solution may be changed (raised or lowered) or multivalent ions, such as calcium, or charged polymers or other macromolecules may be added to the solution.

Suitable peptide amphiphiles, PA segments, PA nanostrcutures, and associated reagents and methods for use in some embodiments herein are described, for example in U.S. Pat. Nos. 8,512,693; 8,450,271; 8,138,140; 8,124,583; 8,114,835; 8,114,834; 8,080,262; 8,063,014; 7,851,445; 7,838,491; 7,745,708; 7,683,025; 7,554,021; 7,544,661; 7,534,761; 7,491,690; 7,452,679; 7,390,526; 7,371,719; 6,890,654; herein incorporated by reference in their entireties. These references are particularly useful for their descriptions of exemplary nanofiber-forming moieties, subsegements thereof, additional functional peptides, and methods of use and preparation of PAs and supramolecular complexes (e.g., nanofibers) thereof.

The characteristics (e.g., shape, rigidity, hydrophilicity, etc.) of a PA supramolecular structure depend upon the identity of the components of a peptide amphiphile (e.g., components of the nanofiber-forming moieties (e.g., lipophilic segment, charged segment, structural segment, etc.). For example, nanofibers, nanospheres, intermediate shapes, and other supramolcular structures are achieved by adjusting the identity of the PA component parts.

In particular embodiments, the compositions and methods herein find use in preventing or reducing inflammation and/or treating inflammatory bowel diseases (e.g., Crohn's disease); however, applications are not so limited. Compositions and methods herein may find use more broadly in tissue regeneration applications (e.g., bowel tissue regeneration), other medical applications, or other non-medical materials applications.

In some embodiments, the hydrophobic segment is a non-peptide segment (e.g., alkyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, aromatic segments, pi-conjugated segments, etc. In some embodiments, the hydrophobic segment comprises an acyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25).

In some embodiments, PAs comprise a structural peptide segment. In some embodiments, the structural peptide segment forms interactions (e.g., beta sheet formation) between PAs within a nanofiber. In some embodiments, structural peptides form the surface of PA nanofibers (e.g., with functional peptides extending therefrom). In some embodiments, peptide amphiphiles comprise a structural peptide or structural peptide sequence with 4 or fewer (e.g., 4, 3, 2, 1, 0, or ranges therebetween) non-conservative substitutions relative to VVVAAA (SEQ ID NO: 6) or VVAA (SEQ ID NO: 7). In some embodiments, peptide amphiphiles comprise an anti-inflammatory peptide or peptide sequence with 4 or fewer (e.g., 4, 3, 2, 1, 0, or ranges therebetween) conservative substitutions relative to VVVAAA (SEQ ID NO: 6) or VVAA (SEQ ID NO: 7). In some embodiments, a structural peptide or structural peptide sequence comprises VVVAAA (SEQ ID NO: 6) or VVAA (SEQ ID NO: 7). In some embodiments, a structural peptide or structural peptide sequence consists of VVVAAA (SEQ ID NO: 6) or VVAA (SEQ ID NO: 7), attached to additional PA-related moieties or segments.

In some embodiments, PAs comprise a charged peptide segment. In some embodiments, the charged peptide segment resides at the surface of a PA, with functional peptides (e.g., AIF, etc.) extending therefrom. In some embodiments, a charged peptide segment may be acidic (e.g., negatively charged), basic (e.g., positively charged), or zwitterionic (e.g., having both acidic and basic residues). Suitable acidic amino acid residues are those having side chains displaying carboxylic acid side chains (e.g., Glu (E), Asp (D), or non-natural amino acids, or peptidomimetics). Other non-natural amino acids displaying carboxylic acid or other acidic groups may find use herein. In some embodiments, the charged peptide segment comprises 2-6 acidic residues selected from glutamate (E) and aspartate (D). In some embodiments, the charged peptide segment comprises $(X^a)_{2-4}$, wherein each $X^a$ is an acidic residue selected from E and D. In some embodiments, the charged peptide segment comprises EEE. Suitable basic amino acid residues are those having amino acid residues having side chains displaying positively-charged acid side chains (e.g., Arg Lys (K), His (H), or non-natural amino acids, or peptidomimetics). Other non-natural amino acids displaying positively-charged acid side chains may find use herein. In some embodiments, the charged peptide segment comprises 2-6 basic residues selected from histidine (H), arginine (R), and lysine (K). In some embodiments, the charged peptide segment comprises $(X^b)_{2-4}$, wherein each $X^b$ is a basic amino acid residue selected from H, R, and K. In some embodiments, a charged peptide segment is a carboxy-rich peptide segment. A carboxy-rich peptide segment may optionally contain one or more additional (e.g., non-acidic) amino acid residues. In some embodiments, a charged peptide segment is a basic peptide segment. A basic peptide segment may optionally contain one or more additional (e.g., non-basic) amino acid residues. A charged peptide segment may comprise one or more non-natural amino acid residues or peptidomimetics with suitable side chains (e.g., basic, acidic, neutral). In some embodiments, a charged segment comprises from about 2 to about 7 amino acids (e.g., 2, 3, 4, 5, 6, 7, or ranges therebetween (e.g., 3-4 amino acids).

In some embodiments, peptide amphiphiles comprise a functional moiety (e.g., AIF, targeting peptide, visualization moiety, etc.). In particular embodiments, a functional moiety is the C-terminal-most segment of the PA. In some embodiments, the functional moiety is attached to the C-terminal end of the charged segment. In other embodiments, a functional moiety is the N-terminal-most segment of the PA. In some embodiments, the functional moiety is attached to the N-terminal end of the charged segment. In some embodiments, the functional moiety is exposed on the surface of an assembled PA structure (e.g., nanofiber). A functional moiety is typically a peptide (e.g., AIF peptide), but is not limited thereto. Examples described in detail herein utilize peptide sequences that produce an anti-inflammatory response; however, other functional peptides and other moieties for achieving desired functionalities will be understood.

In some embodiments, PAs comprise functional peptide segments that provide an anti-inflammatory functionality (e.g., AIF peptides). In some embodiments, AIF peptides are exposed on the surface of PA nanofibers. In some embodiments, peptide amphiphiles comprise an AIF peptide or peptide sequence with 50% or greater sequence identity (e.g., 50%, 60%, 70%, 80%, 90%, 100%, or ranges therebetween) with one of MQMKKVLDS (SEQ ID NO: 1), HDMNKVLDL (SEQ ID NO:2), KVLDPVKG (SEQ ID NO: 3), KVLDGQDP (SEQ ID NO: 4), or DPVKG (SEQ ID NO: 5). In some embodiments, peptide amphiphiles comprise an anti-inflammatory peptide or peptide sequence with 50% or greater sequence similarity (e.g., 50%, 60%, 70%, 80%, 90%, 100%, or ranges therebetween) with one of MQMKKVLDS (SEQ ID NO: 1), HDMNKVLDL (SEQ ID NO: 2), KVLDPVKG (SEQ ID NO: 3), KVLDGQDP (SEQ ID NO: 4), or DPVKG (SEQ ID NO: 5). In some embodiments, peptide amphiphiles comprise an anti-inflammatory peptide or peptide sequence with 5 or fewer (e.g., 5, 4, 3, 2, 1) non-conservative substitutions relative to MQMKKVLDS (SEQ ID NO: 1), HDMNKVLDL (SEQ ID NO: 2), KVLDPVKG (SEQ ID NO: 3), KVLDGQDP (SEQ ID NO: 4), or DPVKG (SEQ ID NO: 5). In some embodiments, peptide amphiphiles comprise an anti-inflammatory peptide or peptide sequence with 8 or fewer (e.g., <8, <7, <6, <5, <4, <3, <2, <1) conservative substitutions relative to MQMKKVLDS (SEQ ID NO: 1), HDMNKVLDL (SEQ ID NO: 2), KVLDPVKG (SEQ ID NO: 3), KVLDGQDP (SEQ ID NO: 4), or DPVKG (SEQ ID NO: 5). In some embodiments, an anti-inflammatory peptide or peptide sequence comprises MQMKKVLDS (SEQ ID NO: 1), HDMNKVLDL (SEQ ID NO: 2), KVLDPVKG (SEQ ID NO: 3), KVLDGQDP (SEQ ID NO: 4), or DPVKG (SEQ ID NO: 5). In some embodiments, an anti-inflammatory peptide or peptide sequence consist of MQMKKVLDS (SEQ ID NO: 1), HDMNKVLDL (SEQ ID NO: 2), KVLDPVKG (SEQ ID NO: 3), KVLDGQDP (SEQ ID NO: 4), or DPVKG (SEQ ID NO: 5), attached to additional PA-related moieties or segments.

In some embodiments, an AIF peptide comprises KVLD (SEQ ID NO: 8). In some embodiments, an AIF peptide comprises at least 75% sequence similarity (e.g., 100% sequence similarity) (e.g., conservative or semi-conservative) with KVLD (SEQ ID NO: 8). In some embodiments, an AIF peptide comprises 6-20 amino acids in length (e.g., 6, 7, 8, 9, 10, 11, 12, 13, 14, 15, 16, 17, 18, 19, 20, or ranges therebetween (e.g., 8-12), etc.) and comprises KVLD (SEQ ID NO: 8) or a tetrapeptide with at least 75% sequence similarity (e.g., 100% sequence similarity) (e.g., conservative or semi-conservative) with KVLD (SEQ ID NO: 8). In some embodiments, an AIF peptide comprises 2-6 amino acid residues preceding a KVLD tetrapeptide (SEQ ID NO: 8) or a tetrapeptide with at least 75% sequence similarity (e.g., 100% sequence similarity) (e.g., conservative or semi-conservative) with KVLD (SEQ ID NO: 8). In some embodiments, an AIF peptide comprises 2-6 amino acid residues following a KVLD tetrapeptide (SEQ ID NO: 8) or a tetrapeptide with at least 75% sequence similarity (e.g., 100% sequence similarity) (e.g., conservative or semi-conservative) with KVLD (SEQ ID NO: 8).

In some embodiments, an AIF peptide comprises: (a) 5 or fewer substitutions relative to MQMKKVLDS (SEQ ID NO: 1), HDMNKVLDL (SEQ ID NO: 2), KVLDPVKG (SEQ ID NO: 3), or KVLDGQDP (SEQ ID NO: 4); and (b) a KVLD tetrapeptide (SEQ ID NO: 8) or a tetrapeptide with at least 75% sequence similarity (e.g., 100% sequence similarity) (e.g., conservative or semi-conservative) with KVLD (SEQ ID NO: 8).

In some embodiments, provided herein are nanofibers and nanostructures assembled from the peptide amphiphiles described herein. In some embodiments, a nanofiber is prepared by the self-assembly of the PAs described herein. In some embodiments, a nanofiber comprises or consists of PAs displaying an AIF peptide. In some embodiments, a nanofiber comprises or consists of PAs displaying an AIF peptide and one or more additional functional moieties (e.g., targeting moiety, visualization moiety, etc.). In some embodiments, the AIF peptides are displayed on the surface of the nanofiber. In some embodiments, the AIF peptides and one or more additional functional moieties (e.g., targeting moiety, visualization moiety, etc.) are displayed on the surface of the nanofiber. In some embodiments, in addition to PAs displaying functional moieties (e.g., AIF peptides, AIF peptides and one or more additional functional moieties (e.g., targeting moiety, visualization moiety, etc.), etc.), filler PAs are included in the nanofibers. In some embodiments, filler PAs are peptide amphiphiles, as described herein (e.g., structural segment, charged segment, hydrophobic segment, etc.), but lacking a functional moiety (e.g., lacking an AIF). In some embodiments, the filler PAs and functional PAs (e.g., AIF PAs) self-assemble into a nanofiber comprising both types of PAs. In some embodiments, nanostructures (e.g., nanofibers) assembled from the peptide amphiphiles described herein are provided.

In some embodiments, nanostructures are assembled from (1) PAs bearing a functional moiety (e.g., AIF peptide, AIF peptides and one or more additional functional moieties (e.g., targeting moiety, visualization moiety, etc.), etc.) and (2) filler PAs (e.g., PAs not-labeled or not displaying a functional moiety (e.g., AIF peptide, AIF peptides and one or more additional functional moieties (e.g., targeting moiety, visualization moiety, etc.), etc.). In some embodiments, nanostructures (e.g., nanofibers) comprise: (i) less than 50% (e.g., 49%, 45%, 40%, 35%, 30%, 25%, 20%, 15%, 10%, 5%, 4%, 3%, 2%, 1%, or any ranges there between) PAs bearing a functional moiety (e.g., AIF peptide, AIF peptides and one or more additional functional moieties (e.g., targeting moiety, visualization moiety, etc.), etc.). In some embodiments, nanostructures (e.g., nanofibers) comprise and at least 2% (e.g., 2%, 3%, 4%, 5%, 10%, 15%, 20%, 25%, 30%, 35%, 40%, 45%, 50%, 55%, 60%, 65%, 70%, 75%, 80%, 85%, 90%, 95%, 98%, or any ranges there between) PAs bearing a functional moiety (e.g., AIF peptide, AIF peptides and one or more additional functional moieties (e.g., targeting moiety, visualization moiety, etc.), etc.). In some embodiments, nanofibers comprise at least 50% (e.g., 50%, 55%, 60%, 65%, 70%, 75%, 80%, 85%, 90%, 95%, 98%, or any ranges there between) filler peptide amphiphiles. In some embodiments, the ratio of PAs bearing a functional moiety to filler PAs determines the density of functional moieties (e.g., AIF peptides, AIF peptides and one or more additional functional moieties (e.g., targeting moiety, visualization moiety, etc.), etc.) displayed on the nanostructure surface.

Figure 7:
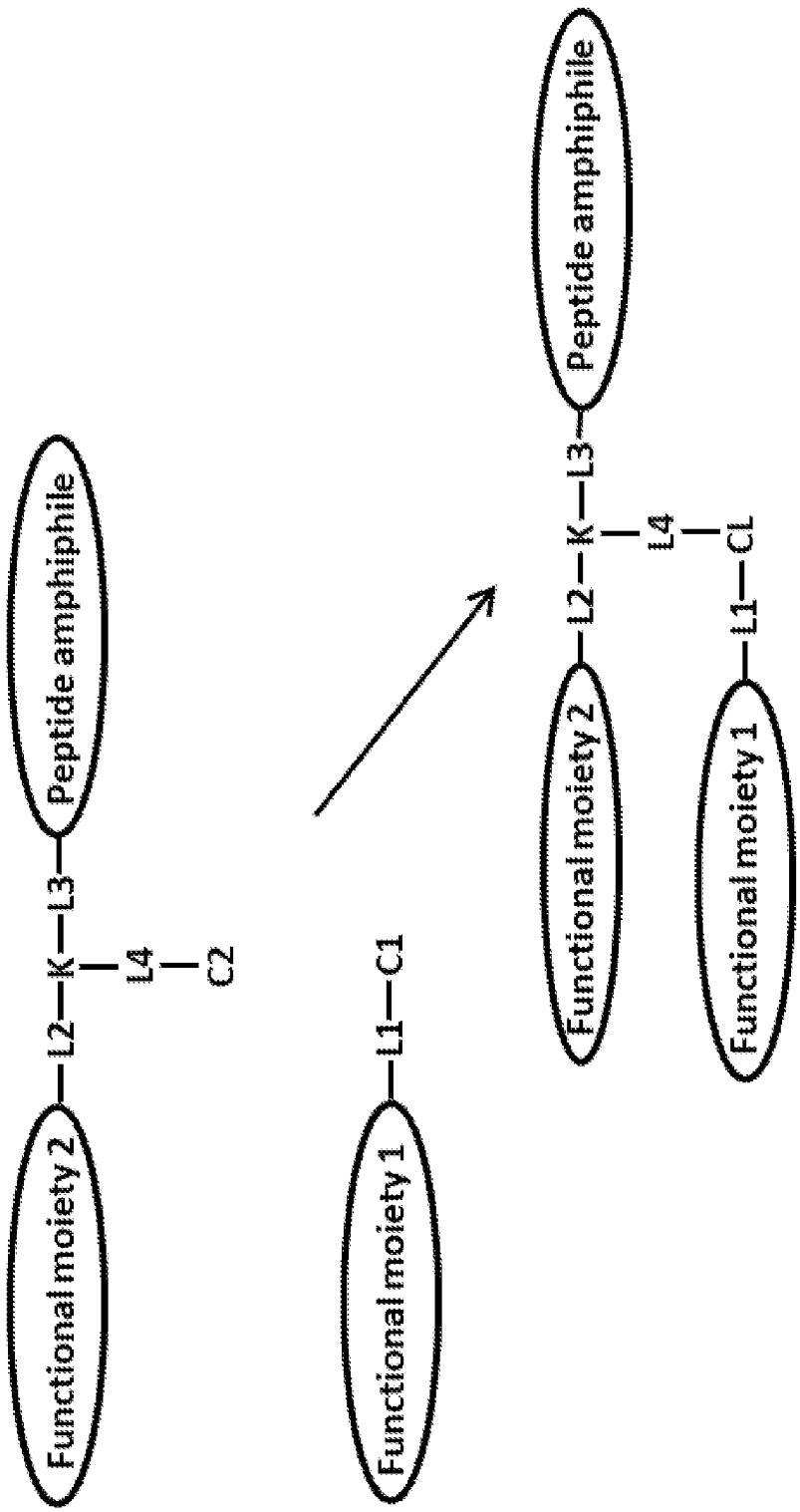
FIG. 7. Schematic depicting an exemplary reaction scheme for synthesis of a branched peptide amphipilie displaying two functional moieties: L1-L4 are linkers (e.g., optionally present), K is a lysine with L4 attached at the lysine side chain, C1 and C2 are clip chemistry reactants, and CL is a clip linkage resulting from the reaction of C1 and C2.
Figure 8:
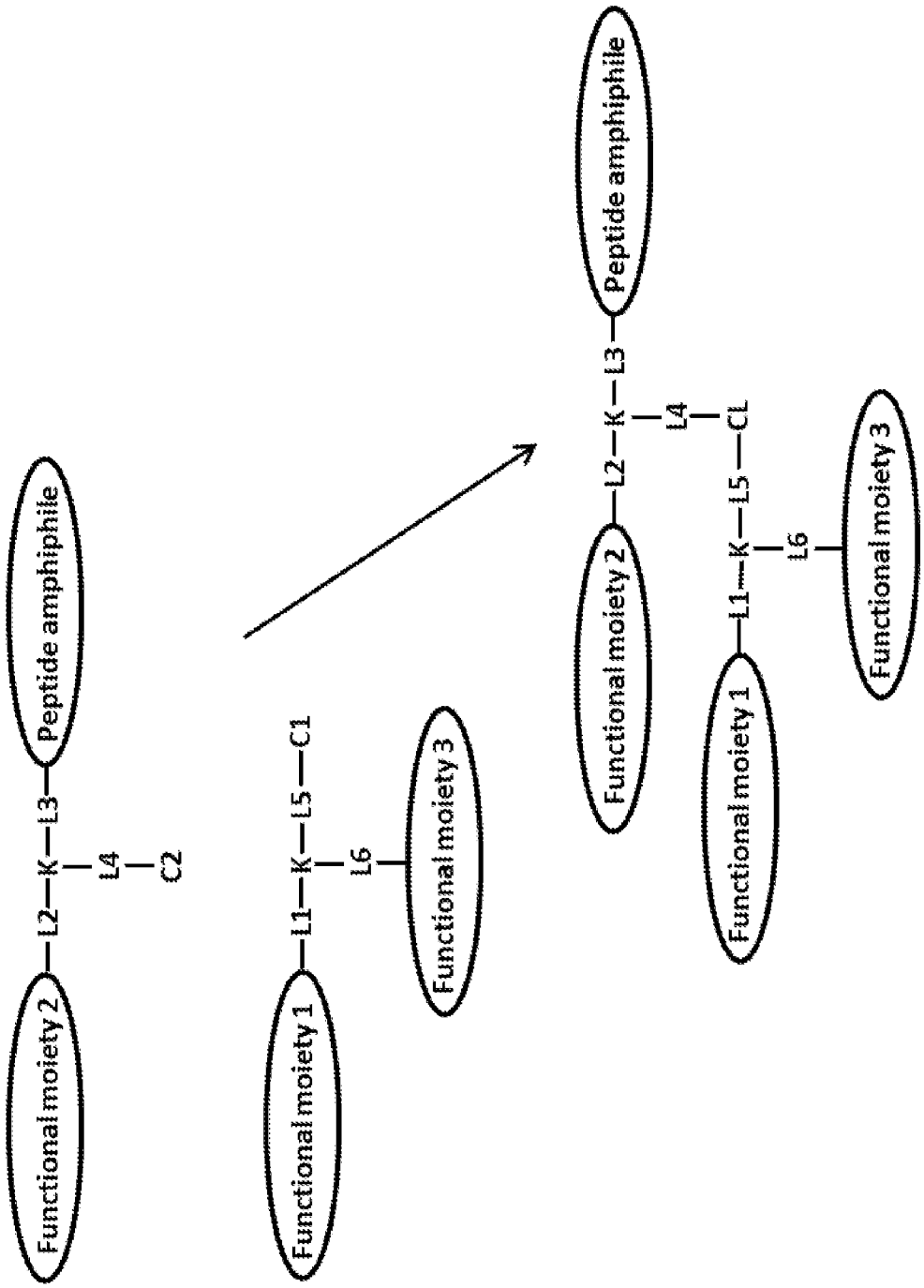
FIG. 8. Schematic depicting an exemplary reaction scheme for synthesis of a branched peptide amphipilie displaying two functional moieties: L1-L6 are linkers L1-L4 are linkers (e.g., optionally present), K is a lysine with L4/L6 attached at the lysine side chain, C1 and C2 are clip chemistry reactants, and CL is a clip linkage resulting from the reaction of C1 and C2.
Figure 9:
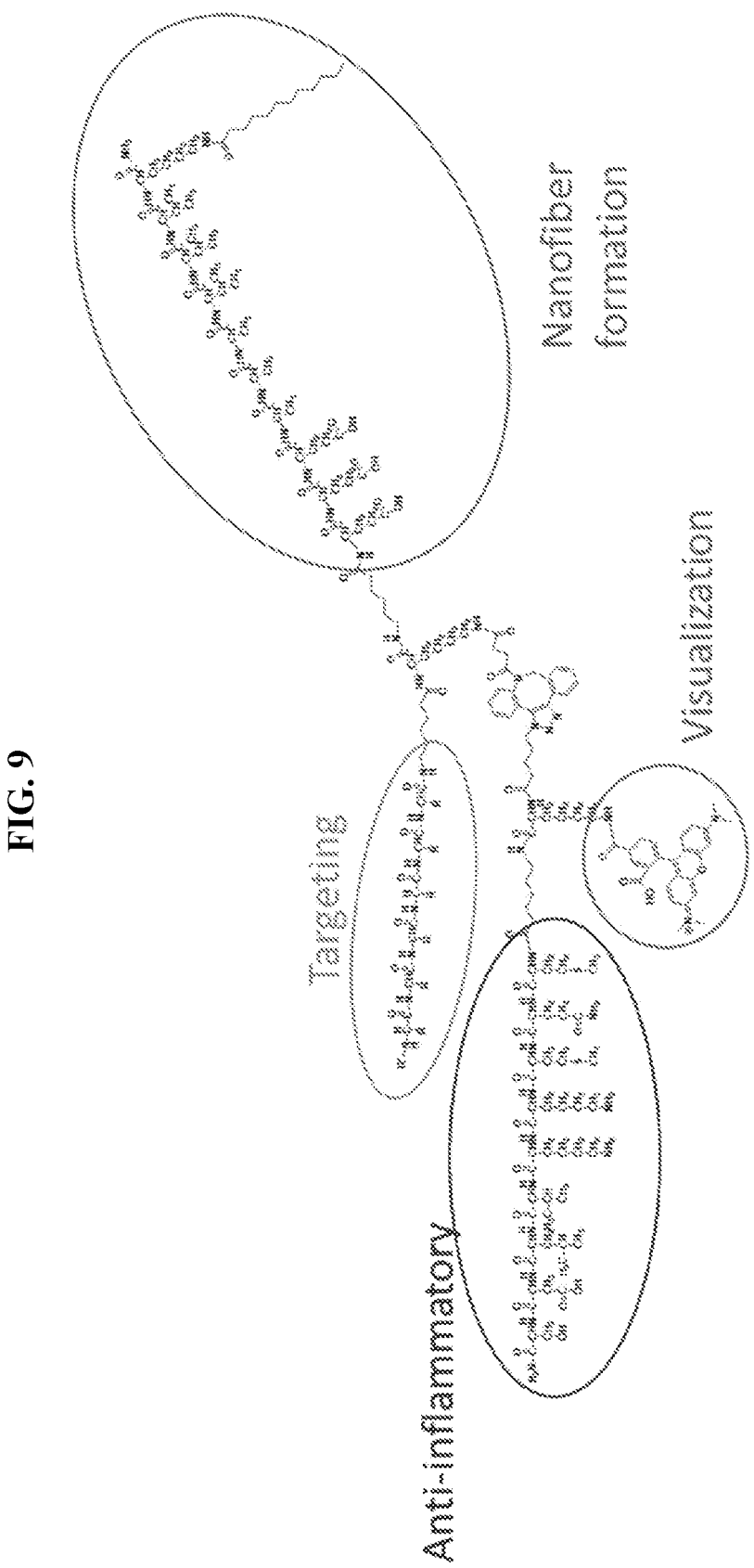
FIG. 9. Exemplary peptide amphiphile displaying an anti-inflammatory peptide, a targeting peptide, and a visualization moiety.

As exemplified in Example 2 and depicted in FIGS. 7-9, certain embodiments herein relate to peptide amphiphiles displaying two or more functional moieties (e.g., AIF peptide and a targeting peptide; AIF peptide, a targeting peptide, and a visualization moiety; therapeutic peptide, targeting peptide, and/or visualization moiety; etc.).

In some embodiments, the self-assembling PAs described herein (e.g., comprising a hydrophobic segment, structural peptide, and charged peptide) display (e.g., attached directly or indirectly (e.g., via a linker) to the charged peptide segment) a functional peptide or functional moiety. In some embodiments, provided herein are systems and methods for the attachment of multiple functional peptides/moieties to a PA (See, e.g., FIGS. 7-9). Such peptide amphiphiles, referred to herein as "branched PAs," retain the capability of the base PA to self-assemble into nanostructures (e.g., nanofibers) and display the functional peptides/moieties on the exterior of the nanostructure.

In some embodiments, branches within the functional portion (i.e., the portion of the nanomolecule attached to the base PA (e.g., attached to the charged peptide)) are formed at lysine residues, or at other amino acids having reactive side chains, or at non-amino acid moieties having three potential reactive groups. In some embodiments, lysine residues provide a branch point by virtue of their three reactive groups (e.g., carboxylic acid, backbone amine, and sidechain amine).

In some embodiments, click chemistry is used to assemble portions of the PA nanomolecules (e.g., see FIGS. 7-8). Examples of complementary paired groups that are well known to undergo "click" chemistry reactions are alkyne-azide, alkyne-nitrile oxide, nitrile-azide and maleimide-anthracene. In examples herein, azidopentanoic acid and benzofuran-2-carboxylic acid provide click pairs (e.g., C1 and C2) for assembly of branched PAs (e.g., via formation of CL ("click linkage")), however, other click pairs may readily be substituted for this exemplary pair.

In some embodiments, the PA nanomolecules described herein comprise various structural/functional portions (e.g., PA or self-assembly, branching, therapeutic (e.g., anti-inflammatory), targeting (e.g., LDT), visualization (e.g., fluorophore), etc. In some embodiments, these structural/functional portions are directly connected to yield a PA nanomolecule within the scope herein. However, in other embodiments, structural/functional portions are connected via any suitable linkers. For example, in the X2-LDT-AIF1-PA nanostructure described in Example 2, several hexanamide linkers are used to connect various structural/functional portions. Other linkers are within the scope herein. For example, a linker between two structural/functional portions may comprise a peptide linker (e.g., GG) or non-peptide linker (e.g., alkyl chain (e.g., 1-10 carbons in length), PEG, heteroalkyl chain (e.g., 1-10 atoms in length, a substituted (e.g., NH, OH, C=O, etc.) alkyl or heteroalkyl chain, etc.

In some embodiments, PA nanomolecules described herein display one or more (e.g., 1, 2, 3, 4, 5, 6, or more) functional moieties. In some embodiments, functional moieties are peptides (e.g., AIF peptides, LDT peptides, etc.). In some embodiments, functional moieties are non-peptide moieties (e.g., fluorophores, small molecule drugs, targeting ligands, etc.).

In some embodiments, a functional moiety is a therapeutic moiety. In some embodiments, a therapeutic moiety is a therapeutic peptide. In some embodiments, a therapeutic peptide is an anti-inflammatory peptide. In other embodiments, a therapeutic moiety is any peptide or small molecule that exhibits a therapeutic effect when exposed to and/or delivered to a cell, tissue, organ, system, or subject. Experiments conducted during development of embodiments herein, as well as experiments with other PAs, demonstrate that peptide amphiphiles and self-assembled nanostrcutres thereof exhibit similar or enhanced effects of the therapeutic peptides or other moieties displayed thereon. As such, while the examples herein demonstrate the utility of branched PAs with specific anti-inflammatory therapeutic peptides, embodiments herein also find use with other peptides (e.g., other anti-inflammatory peptide, other targeting peptides, etc.) and small molecule moieties (e.g., other fluorophores).

Targeting Moieties

In some embodiments, PA nanomolecules described herein display a targeting moiety. In some embodiments, a targeting moiety allows localization of a PA (or nanofiber thereof) to a specific treatment site (e.g., bowels or a subject, site of inflammation, etc.). In some embodiments, a targeting moiety allows systemic delivery of a composition herein, followed by localization of the composition to a desired treatment site. In some embodiments, a targeting moiety is a targeting peptide. In some embodiments, a targeting peptide comprises LDT.

In some embodiments, PA nanomolecules described herein display a visualization moiety. In some embodiments, a visualization moiety allows for detection of the PA within a cell, tissue, subject, etc. In some embodiments, a visualization moiety allows a user (e.g., clinician) to determine is a PA (or nanofiber thereof) is localizing to the treatment site. In some embodiments, a visualization moiety is a fluorophore (e.g., small molecule fluorophore). Exemplary fluorophores for use in embodiments herein include, but are not limited to, fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine, 5-(2'-aminoethy)aminonaphthalene-1-sulfonic acid (EDANS), Alexa dyes, etc.

Compositions and methods herein find use in a variety of applications. In particular, the PAs herein are administered (e.g., systemically or locally) for the treatment of inflammation-related conditions/diseases/disorders. In some embodiments, the PAs herein are administered (e.g., systemically or locally) for the treatment of inflammation-related conditions/diseases/disorders in the bowel of a subject. In some embodiments, pharmaceutical compositions comprising the PAs herein are administered are administered topically or by injection to the site of treatment (e.g., site of inflammation (e.g., lesions)) in the bowels. In some embodiments, an endoscope (e.g., inserted through the rectum) is used to administer the PAs herein to treatment sites within the bowels. In some embodiments, PAs herein are formulated for rectal administration (e.g., as a suppository). In some embodiments, pharmaceutical compositions comprising the PAs herein are administered rectally (e.g., as a suppository). In other embodiments, PAs herein are administered systemically (e.g., orally, intravenously, etc.). In some embodiments, methods are provided herein for the treatment of one or more of irritable bowel syndrome (IBS), uncontrolled diarrhea-associated Irritable Bowel Syndrome (dIBS), Crohn's disease, traveler's diarrhea, ulcerative colitis, enteritis, small intestinal bacterial overgrowth, chronic pancreatitis, pancreatic insufficiency, colitis, diverticular disease, fibromyalgia, systemic lupus erythematosus, hepatic encephalopathy, and/or symptoms (e.g., inflammation, lesions, etc.) related thereto. In some embodiments, the PAs described herein (or nanofibers thereof, or pharmaceutical compositions thereof) are administered to a subject suffering from one of the aforementioned conditions. In some embodiments, the PAs described herein are co-administered and/or co-formulated with other agents for the treatment of bowel diseases.

EXPERIMENTAL

Example 1

AIF-PA

Anti-Inflammatory Peptide Amphiphile Synthesis

Anti-inflammatory peptide amphiphiles (AIF-PAs) were synthesized utilizing standard fluoroen-9-ylmethoxycarbonyl (Fmoc) solid phase peptide synthesis (SPPS) procedures. The AIF-PAs were synthesized from the C terminus to N terminus, with Rink Amide MBHA [4-(2',4'-Dimethoxyphenyl-Fmoc-aminmethyl)-phenoxyacetamido-methylbenzhydryl amine resin] at the C terminus as the solid state support for the addition of Fmoc-protected AA. The Fmoc group was removed by agitating the resin in a solution of 30% piperidine in dimethylformamide (DMF) (v/v) for 10 minutes. This step was performed twice at the beginning of each AA coupling step. This was followed by a wash with dichloromethane (DCM), two washes with DMF, and finally two final washes in DCM. A Ninhydrin test was performed to confirm the presence of an N-terminus free amine indicated by a positive color change to purple. The AA coupling cocktail consisted of a 4× molar excess of the Fmoc AA, 3.95× molar excess of O-Benzotriazole-N,N,N',N-tetramethyl-uronium-hexafluoro-phosphate (HBTU), and a 6× molar excess of N,N-diisopropylethylamine (DIEA) all relative to the resin. The AA, HBTU, and DIEA were dissolved in approximately 20 mL of DMF. Once the Ninhydrin test confirmed the presence of free amino termini, the AA coupling cocktail was added to the resin and agitated for a minimum of 3 hours. Following agitation, the resin was washed thoroughly with DMF 3× for approximately one minute per wash and subsequently washed with DCM twice. A final Ninhydrin test was performed to confirm the AA had been coupled successfully indicated by a no color change. The remaining AA was added. Following the addition of the AA sequence, a palmitic acid (C16) tail was coupled for 2 hours at 4× molar excess with 3.95× and 6× molar excess of HBTU and DIEA, respectively, dissolved in a 20:80 mixture of DCM:DMF.

To cleave the finished AIF-PA from the resin, a solution containing 95% trifluoroacetic acid (TFA), 2.5% triisopropylsilane (TIS), and 2.5% nanopure water was mixed with the resin and agitated for at least 3 hours. The solution was isolated from the resin into a 500 mL round bottom flask, and the resin was washed once with DCM. The TFA was removed using a rotary evaporator (R-210; Buchi Analytical Inc.) at 50° C. Cold diethyl ether was added to remove soluble protecting groups remaining after cleaving and precipitate the AIF-PAs. The AIF-PA diethyl ether solution was centrifuged and decanted, leaving only the AIF-PA precipitate, which was then dried under vacuum for 2 days. Following cleavage, the AIF-PAs were purified via RP-HPLC (Varian Prostar; Varian Inc.) under either acidic (C-18 Atlantis Column; Waters Corp.) or basic (C-18 Gemini Column; Phenomenx Inc.) conditions based on the net charge of the complete AIF-PA at physiological pH. Purification was monitored by UV/Vis spectroscopy at 220 nm and 325 nm. Fractions of interest were confirmed to contain the target AIF-PA via mass spectrometry (6510 Q-TOF LC/MS 1200 Series; Agilent Technologies). Following purification, the AIF-PAs were subject to rotary evaporation before being lyophilized (FreeZone Plus 6; Labconco Corp.) for 3 days. Dried samples were stored at −20° C. until needed. Exemplary AA sequences of the AIF-PAs utilized is certain experiments conducted during development of embodiments herein include AIF-PA1: $C_{16}$-VVVAAAEEEMQMKKVLDS (SEQ ID NO: 10) and AIF-PAC (Control): $C_{16}$-VVVAAAEEEKLMSQKMVD (SEQ ID NO: 11).

Treatment of Inflammatory Intestinal Lesions in an Animal Model of Ileitis

Figure 2:
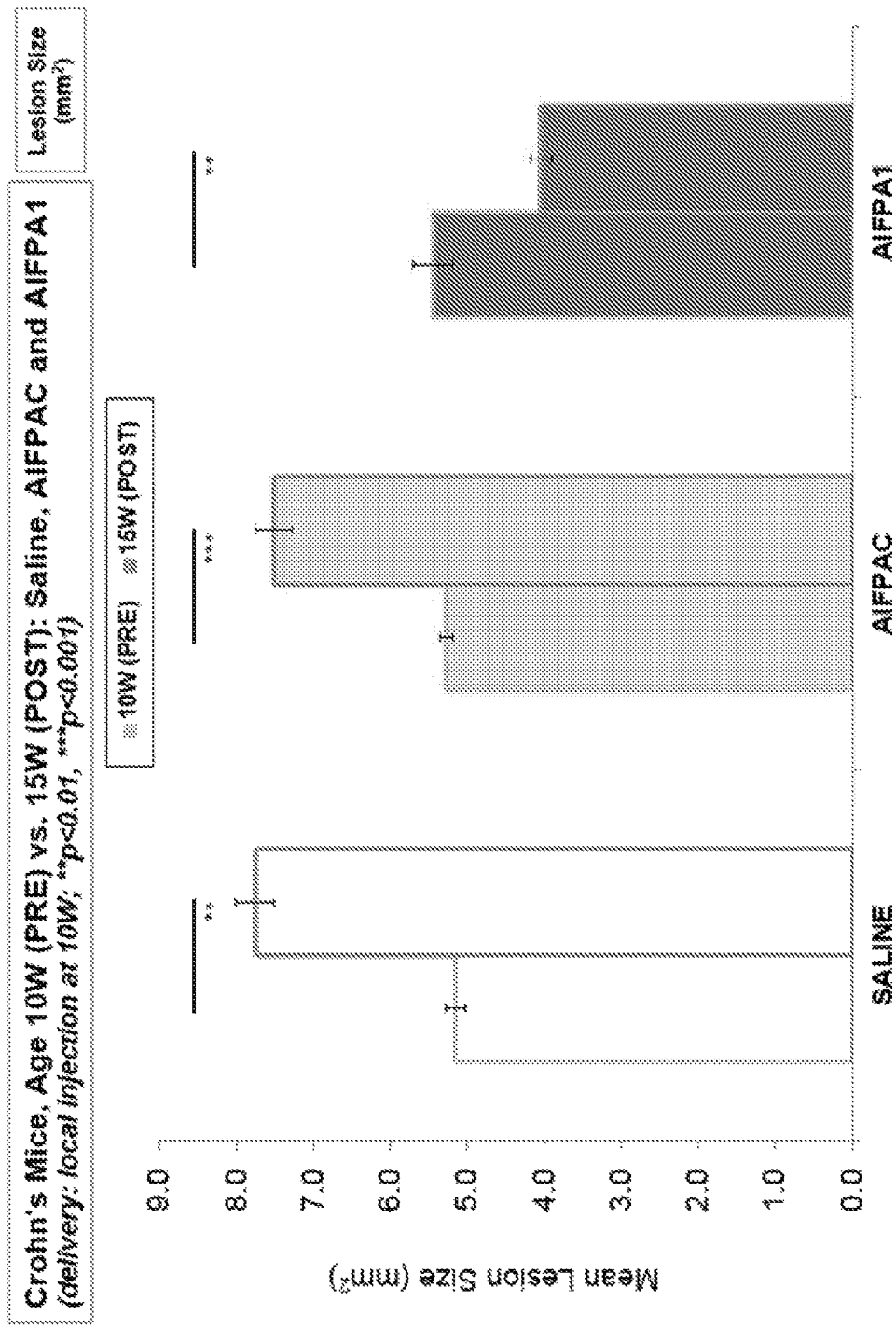
FIG. 2. Inflammatory intestinal lesion size following treatment in SAMP1/YitFcsJ mice (Crohn's mice). Following direct treatment injection of either saline, AIF-PAC or AIF-PA1 into inflamed intestinal lesions of SAMP1/YitFcsJ mice, the mice were evaluated for a change in intestinal lesion size 5 weeks post-injection. Data demonstrate a statistically significant decrease in lesion size ($mm^2$) in AIF-PA1 treated animals compared to AIF-PAC and saline injected control animals pre-versus post-injections.
Figure 3:
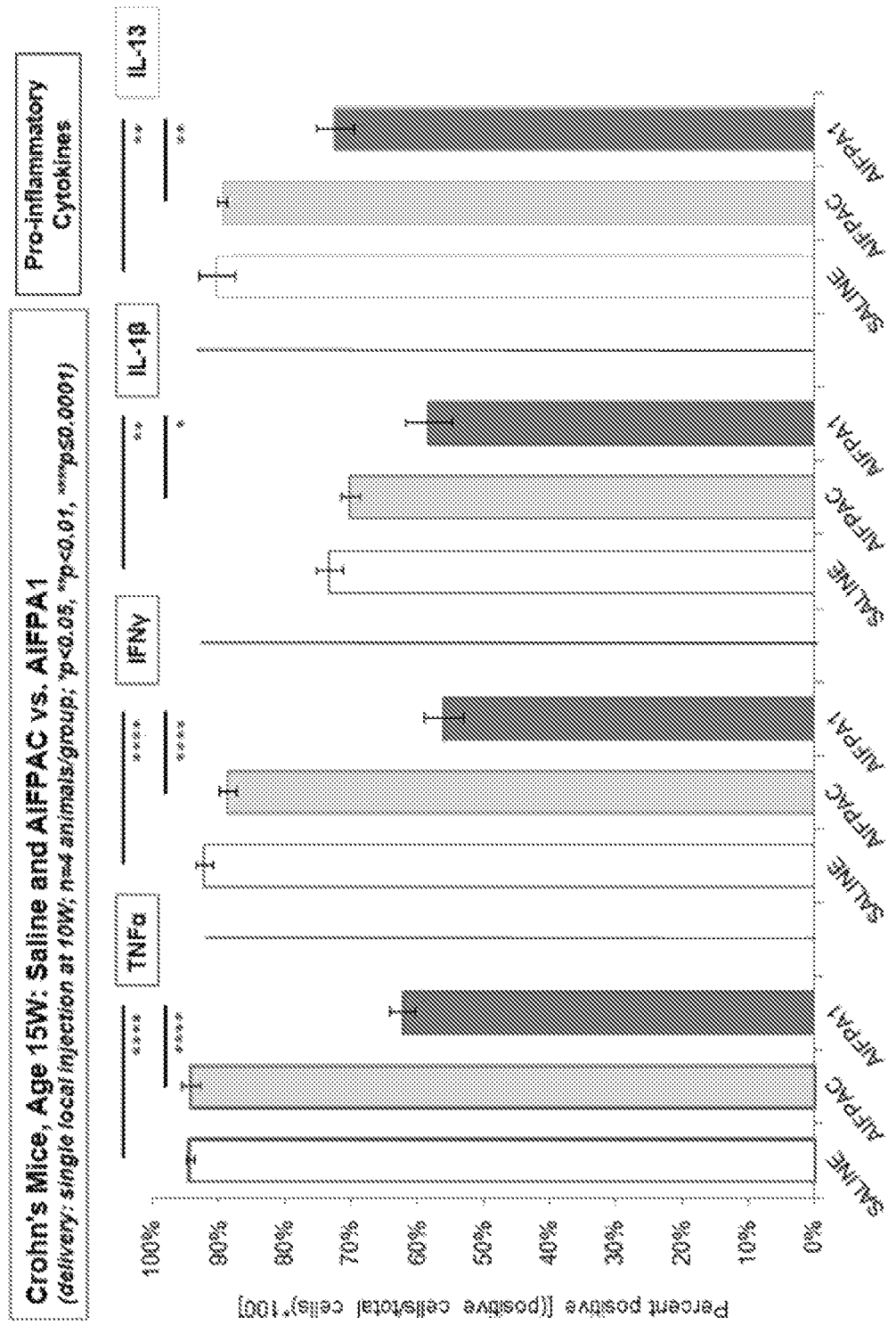
FIG. 3. Cytokine expression following treatment in SAMP1/YitFcsJ mice (Crohn's mice). Following direct treatment injection of either saline, AIF-PAC or AIF-PA1 into inflamed intestinal lesions of SAMP1/YitFcsJ mice, the mice were evaluated for the expression of specific inflammatory cytokines tumor necrosis factor-alpha (TNFα), interferon gamma (IFNγ), interleukin-1 beta (IL-1β), and interleukin-13 (IL-13). These cytokines are pro-inflammatory in nature and are involved with the deterioration of intestinal tissue upon prolonged exposure. Data demonstrate a statistically significant decrease in pro-inflammatory cytokines, TNFα, IFNγ, IL-1β, and IL-13 in AIF-PA1 treated animals compared to AIF-PAC and saline injected control animals.

The SAMP1/YitFcsJ mouse closely mimics human Crohn's disease (CD) by exhibiting spontaneous formation of inflammatory-based intestinal lesions and other symptoms of intestinal ileitis. This pre-clinical model demonstrates close to 100% penetrance at an early stage in the mouse lifecycle and is amenable to data extrapolation to the human condition. In order to treat inflammatory lesions that have formed in the intestinal tracts, the following was performed:

Mice (10 weeks of age, female) were brought to the operating room where they were weighed, the abdomen shaved to remove hair, and given Buprenorphine (0.05 mg/kg) administered subcutaneously. At the time of surgery, anesthesia was induced with isoflurane (2%) with 02 and the mice were prepped with providine-iodine three times prior to initiating the operation. All mice received a 100 mg/kg dose of IP piperacillin/tazobactam IP followed by a midline abdominal incision (1.0-1.5 cm) made in the linea albea to gain access to the peritoneum. The intestines were then identified in the peritoneal cavity. Following intestinal exposure and identification of intestinal lesions, the anti-inflammatory peptide amphiphiles, [AIF-PA1 (treatment; 2 wt/%) or AIF-PAC (control; 2 wt/%)] or saline (control) were independently injected (20-40 µl) into multiple lesions of the several SAMP1/YitFcsJ mice. Following the surgical procedure, organs were relocated to their original anatomical positions. The abdomen was closed in 2 layers (muscle and skin) with 3-0 PDS suture. After recovery, they were placed back into cages with non-edible bedding and provided ad lib water and liquid diet for the first 7 post-operative days and then returned to ad lib chow. Animals were sacrificed at the 15 weeks of age. Animals were euthanized 5 weeks post-surgery and intestinal tissue was explanted, sectioned and stained with relevant inflammation based antibodies. Tissue samples were subsequently quantified, and the results are depicted in FIGS. 1-3.

Example 2

AIF-PA/LDT

Anti-Inflammatory Peptide Amphiphile Synthesis

Peptide synthesis was carried out using a CEM Liberty or CEM Liberty Blue microwave-assisted peptide synthesizer via standard 9-fluorenyl methoxycarbonyl (Fmoc) solid-phase peptide synthesis on rink amide MBHA resin. Peptides were cleaved from the resin using standard solutions (95% TFA, 2.5% water, 2.5% triisopropylsilane (TIS)), precipitated with cold ether and then purified by reverse-phase HPLC on a Waters Prep150 or Shimadzu Prominence HPLC using a water/acetonitrile (each containing 0.1% v/v trifluoroacetic acid or 0.1% NH$_4$OH) gradient. Eluting fractions containing the desired peptide were confirmed by mass spectrometry using an Agilent 6520 QTOF LCMS. Confirmed fractions were pooled and the acetonitrile was removed by rotary evaporation before freezing and lyophilization. Purity of lyophilized products was tested by LCMS on an Agilent 6520 QTOF LCMS.

```
                                                 (SEQ ID NO: 10)
Synthesis of Palmitoyl-VVVAAAEEEMQMKKVLDS (AIF-
  PA1)
and
                                                  (SEQ ID NO: 9)
Palmitoyl-VVVAAAEEE.
```

Palmitic acid was used for the addition of the palmitoyl moiety directly to the N-terminus using these same conditions. After purification, lyophilized fractions were characterized by LCMS. AIFPA1 was determined to be >95% pure by absorbance at 220 nm (MS-calc. 2213.3 m/z, obs. 2214.0 m/z) as well as the palmitoyl-VVVAAAEEE (SEQ ID NO: 9) (MS-calc. 1152.7 m/z, obs. 1152.6 m/z).

```
Synthesis of peptides AIF1 (azidopentanoic acid-K-
[TAMRA]-Ahx-MQMKKVLDA (SEQ ID NO: 1))
and AIF6 (azidopentanoic acid-K-[TAMRA]-Ahx-KLMSQKMVD
(SEQ ID NO: 12)).
```

The base peptide sequences were made by automated peptide synthesis (H2N-K(Mtt)-Ahx-MQMKKVLDS (SEQ ID NO: 1) and H2N-K(Mtt)-Ahx-KLMSQKMVD (SEQ ID NO: 12)) for AIF1 and AIF6 respectively and the mass was confirmed in each case before going forward (MS-calc. 1318 m/z, obs. 1318 m/z). To the peptides on resin, was then added 2 equiv. (relative to peptide) of 5-azidopentanoic acid, HBTU (1.9 equiv.) and DIEA (4 equiv.) in DMF. After 3 hours the resin was rinsed and a test cleavage was performed to confirm addition (MS-calc. 1443 m/z, obs. 1443 m/z). The Mtt (4-methyltrityl) protecting group was then removed from the lysine near the N-terminus using standard protocols (3% TFA, 92% DCM, 5% TIS) before adding 5-(and -6)-Carboxytetramethylrhodamine (TAMRA) using 2 equiv. (relative to peptide), HBTU (1.9 equiv.) and DIEA (4 equiv.). TAMRA addition was confirmed by test cleavage (MS-calc. 1857 m/z, obs. 1857 m/z) before full cleavage and purification by HPLC.

```
Synthesis of X2-LDT-PA (Benzofuran-2-carboxylic
acid-LDT-Ahx-K(DBCO)-Ahx-EEEAAAVVV-K(lauryl
(SEQ ID NO: 13)).
```

Low loading (0.35 mmol/g) rink amide MBHA resin was Fmoc deprotected (20% 4-methylpiperidine in DMF) before adding Fmoc-K(Mtt)-OH, 2 equiv., HBTU (1.9 equiv.) and DIEA (4 equiv.), which was allowed to shake for 4 hours at room temperature (rt). The Mtt protecting group was then removed as described above before adding lauric acid using 4 equiv., HBTU (3.9 equiv.) and DIEA (8 equiv.) in DMF for 6 hours. The remainder of the base peptide was then synthesized using automated peptide synthesis resulting in H2N-LDT-Ahx-K(Mtt)-Ahx-EEEAAAVVV-K(lauryl) (SEQ ID NO: 13) that was tested for completion by test cleavage (MS-calc. 1918 m/z, obs. 1918 m/z). Benzofuran-2-carboxylic acid (X2) was then added using 4 equiv., HBTU (3.9 equiv.) and DIEA (8 equiv.) in DMF for 4 h and the mass was confirmed by test cleavage (MS-calc. 2053 m/z, obs. 2053 m/z). The Mtt protecting group was then removed and DBCO-Acid (Click Chemistry Tools) 2 equiv., HBTU (1.9 equiv.) and DIEA (4 equiv.) was then added in DMF for 4 h to overnight and the mass of the resulting final product was confirmed by test cleavage (MS-calc. 2339 m/z, obs. 2340 m/z). LDT=leucine-aspartic acid-threonine tripeptide.

Synthesis of AIF-PA1/LDT and AIFC-PA6/LDT.

To the X2-LDT-PA on resin, was added peptides AIF1 or AIF6 (approx. 0.33 equiv.) in DMF. The reaction was monitored over time using test cleavages looking for the disappearance of the starting material peak at 2339 m/z and the appearance of the product peak (MS-calc. 4196.2 m/z, obs. 4196.8 m/z). This reaction typically took 3-4 days shaking at room temperature at which point the decrease of the 2339 m/z starting material stopped decreasing. The final product peptide was then cleaved from the resin and purified by HPLC. Purity of the lyophilized product was determined by LCMS to be >90% by absorbance at 220 nm.

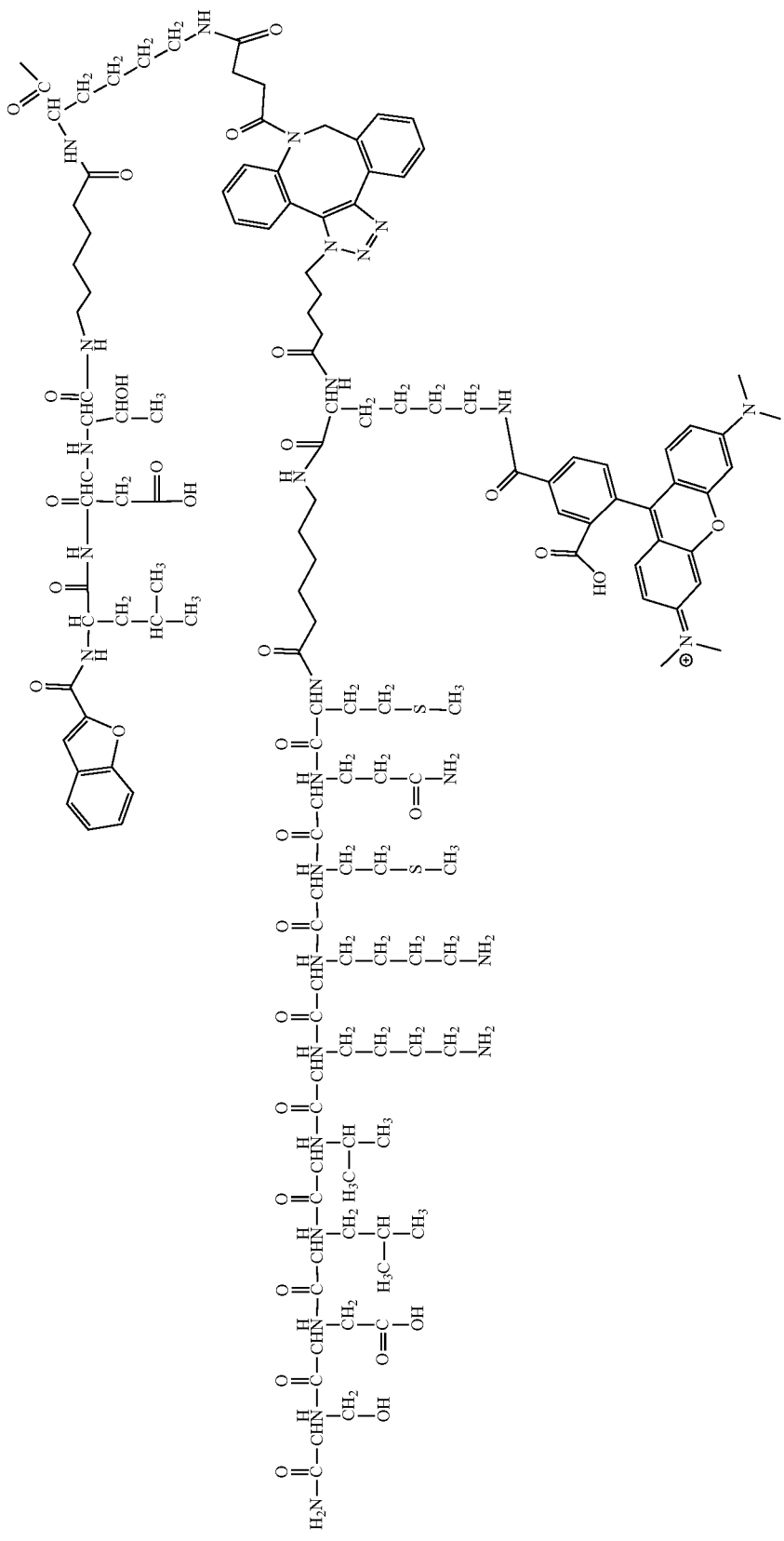

-continued
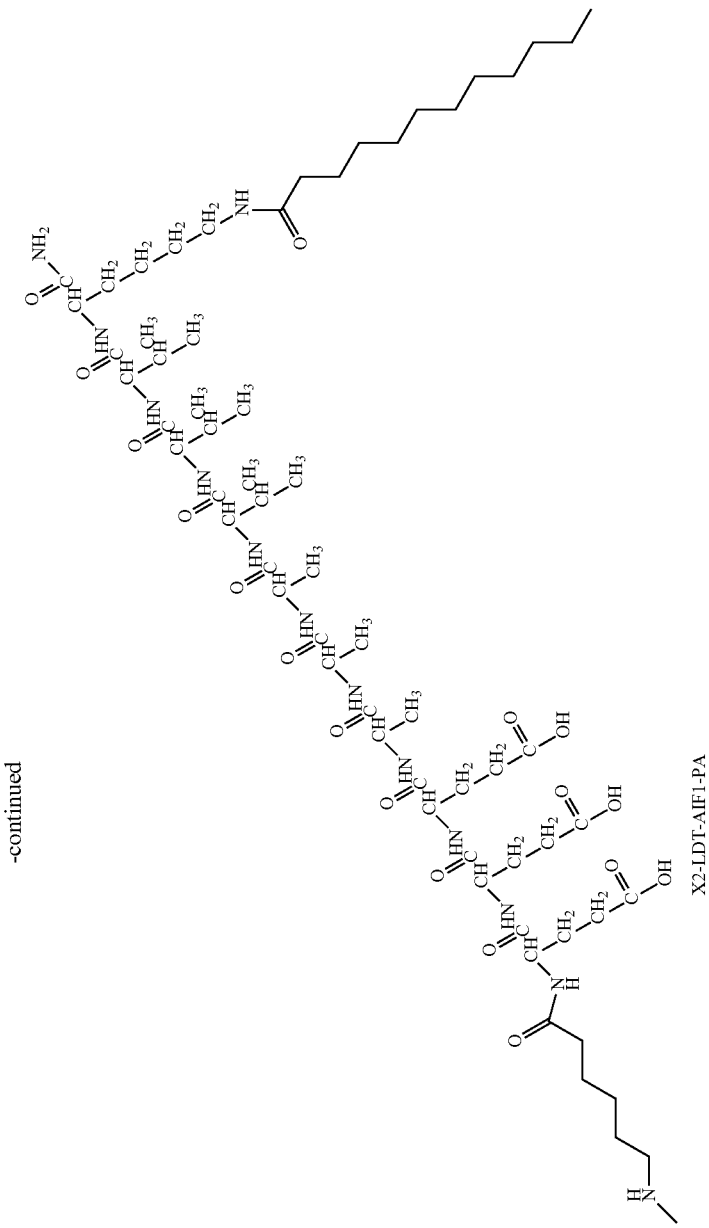
X2-LDT-AIF1-PA

-continued
X2-LDT-AlF6-PA
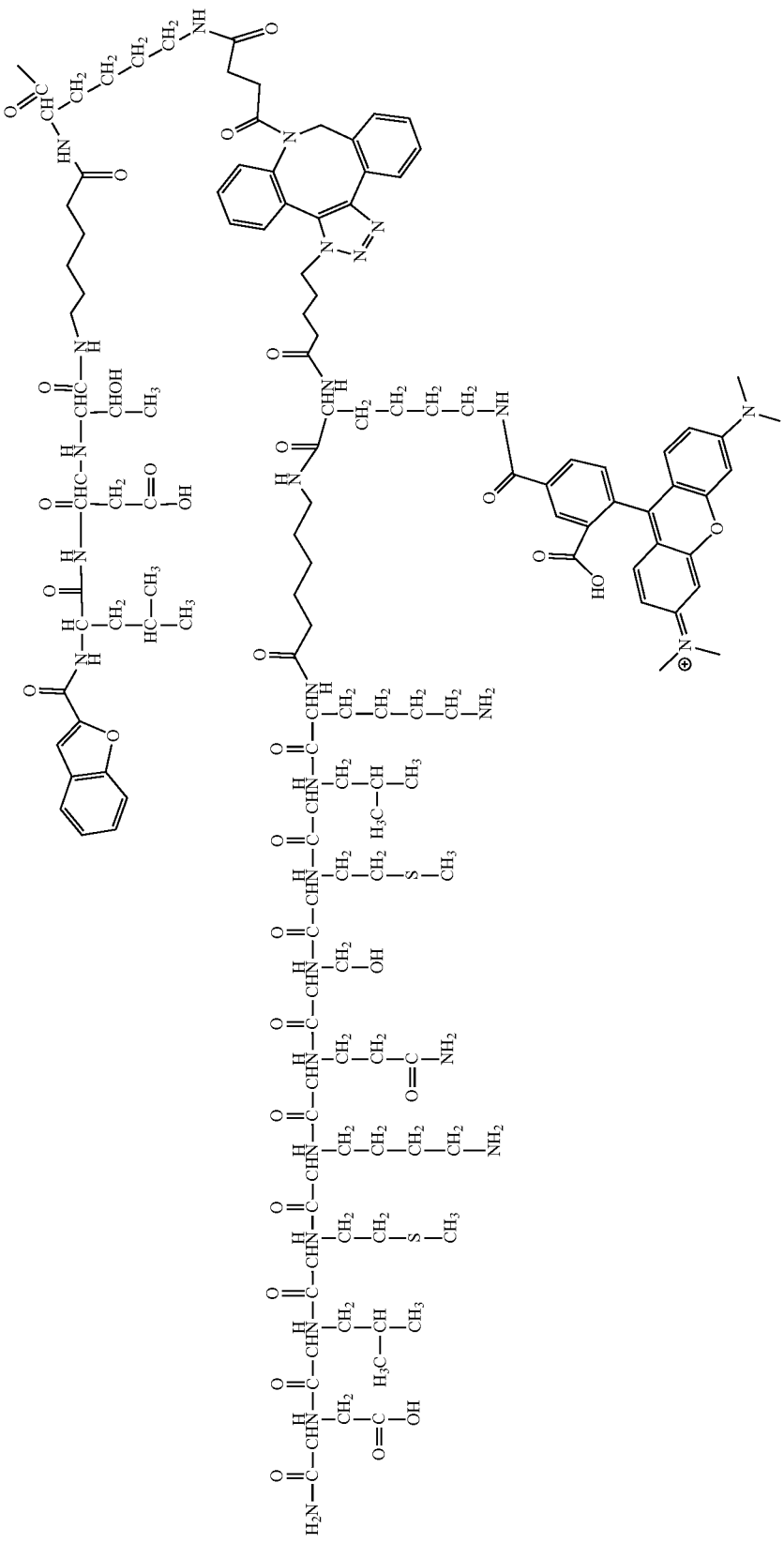

-continued
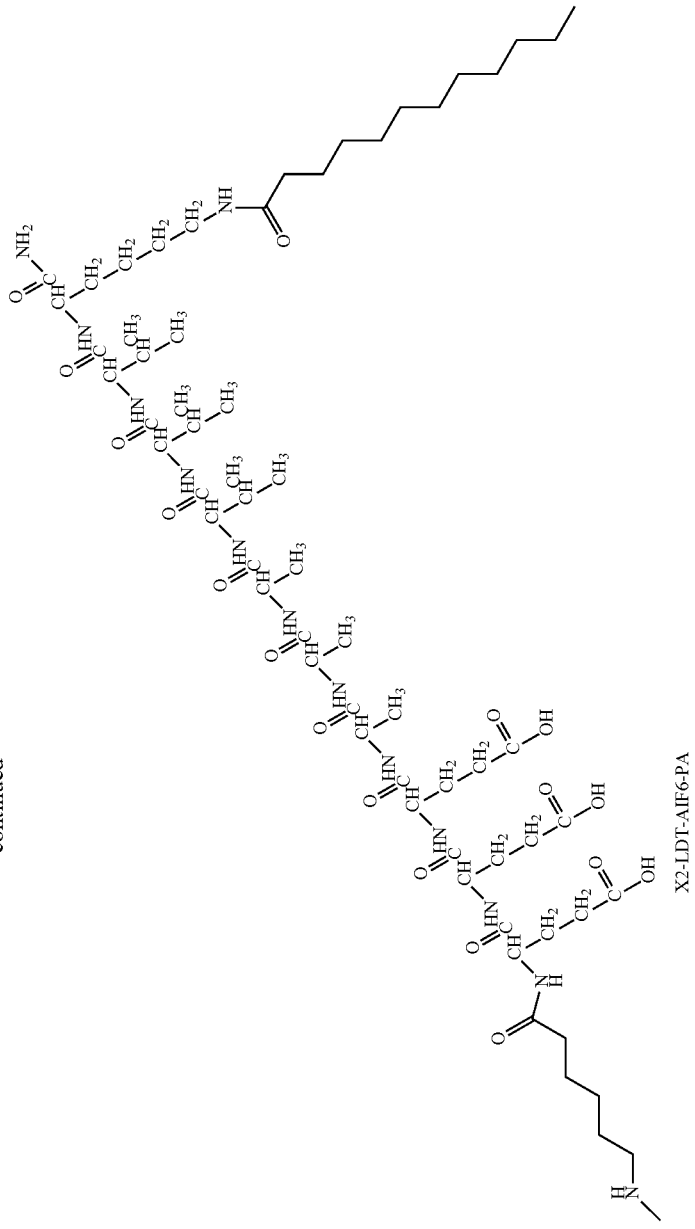
X2-LDT-AIF6-PA

Treatment of Inflammatory Intestinal Lesions in an Animal Model of Ileitis

Figure 4:
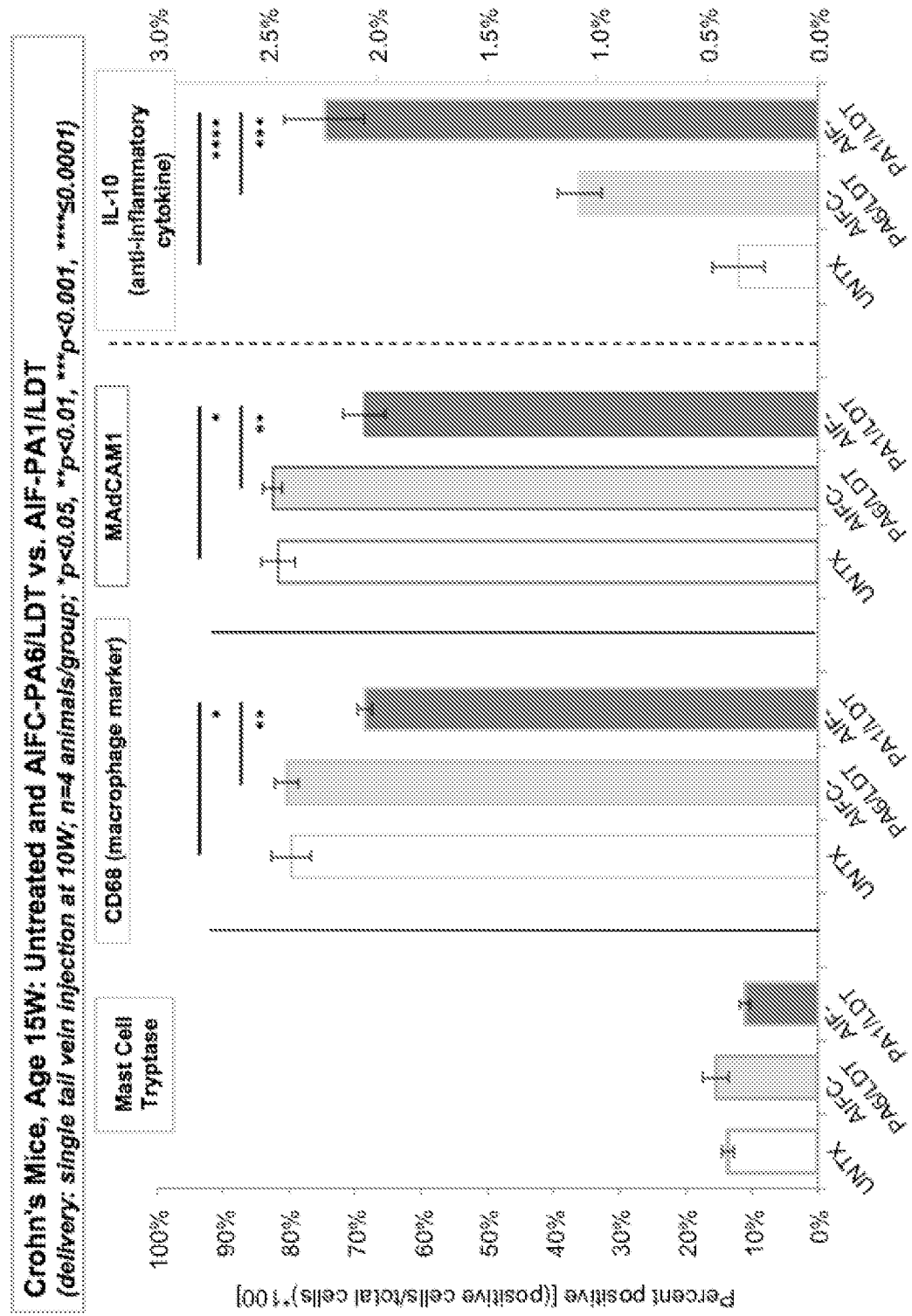
FIG. 4. Cell/marker expression following treatment of SAMP1/YitFcsJ mice (Crohn's mice). Following systemic injection of either AIFC-PA6/LDT or AIF-PA1/LDT into SAMP1/YitFcsJ mice, intestinal tissue from animals was evaluated for the expression of specific inflammatory cell epitopes [mast cell tryptase (mast cells); CD68 (macrophages)], a marker associated with ileitis based inflammation (MAdCAM1), and the anti-inflammatory cytokine interleukin-10 (IL-10). Data demonstrate a statistically significant decrease in CD68, and MAdCAM1 with a concomitant increase in anti-inflammatory cytokine IL-10 in AIF-PA1/LDT treated animals compared to untreated controls.
Figure 5:
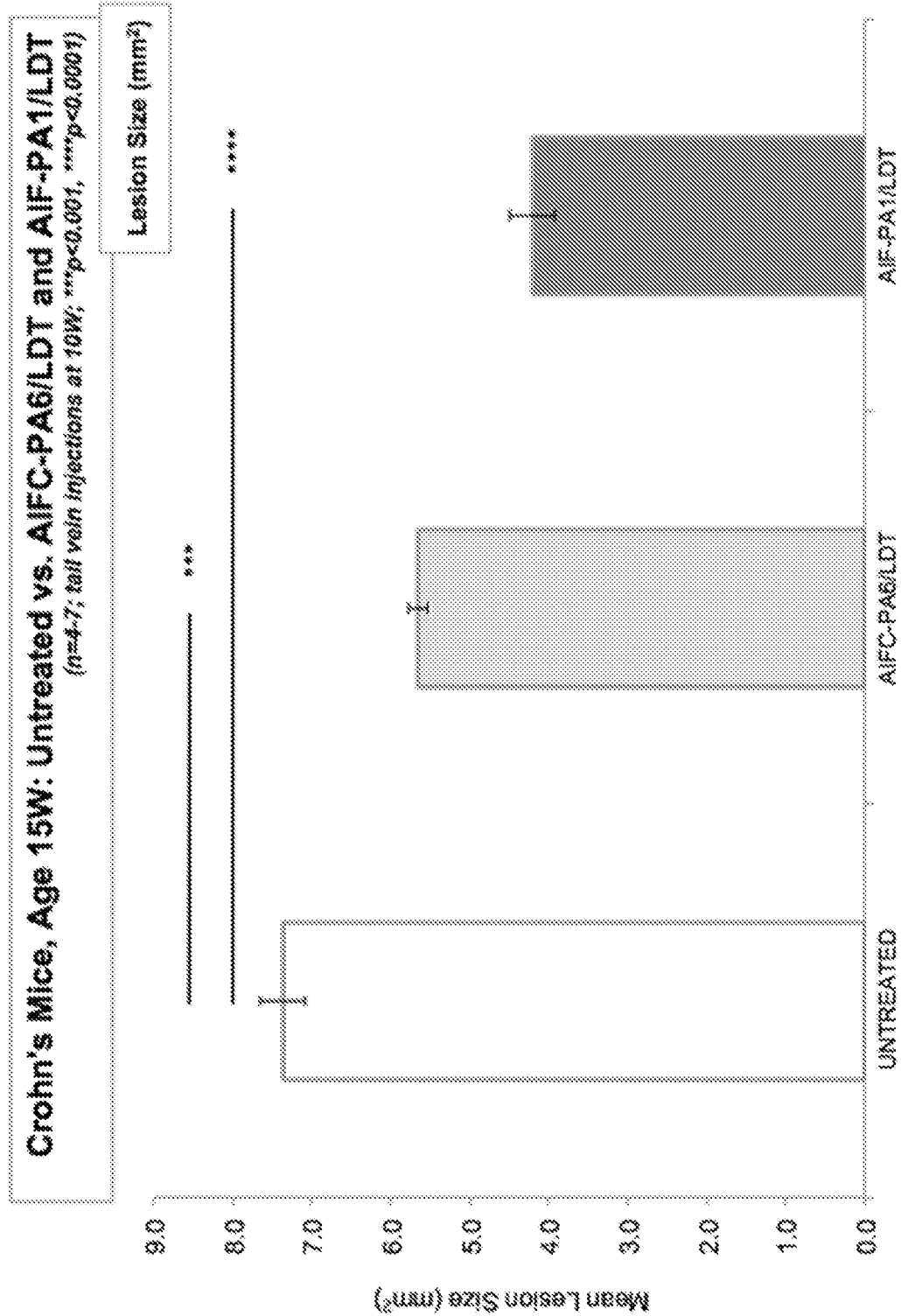
FIG. 5. Inflammatory intestinal lesion size following treatment in SAMP1/YitFcsJ mice (Crohn's disease mice). Following the independent systemic injection of either AIFC-PA6/LDT (control) or AIF-PA1/LDT, mice were evaluated for a change in intestinal lesion size 5 weeks post-injection. Data demonstrate a statistically significant decrease in lesion size ($mm^2$) in AIF-PA1/LDT treated animals compared to AIFC-PA6/LDT and untreated control animals.
Figure 6:
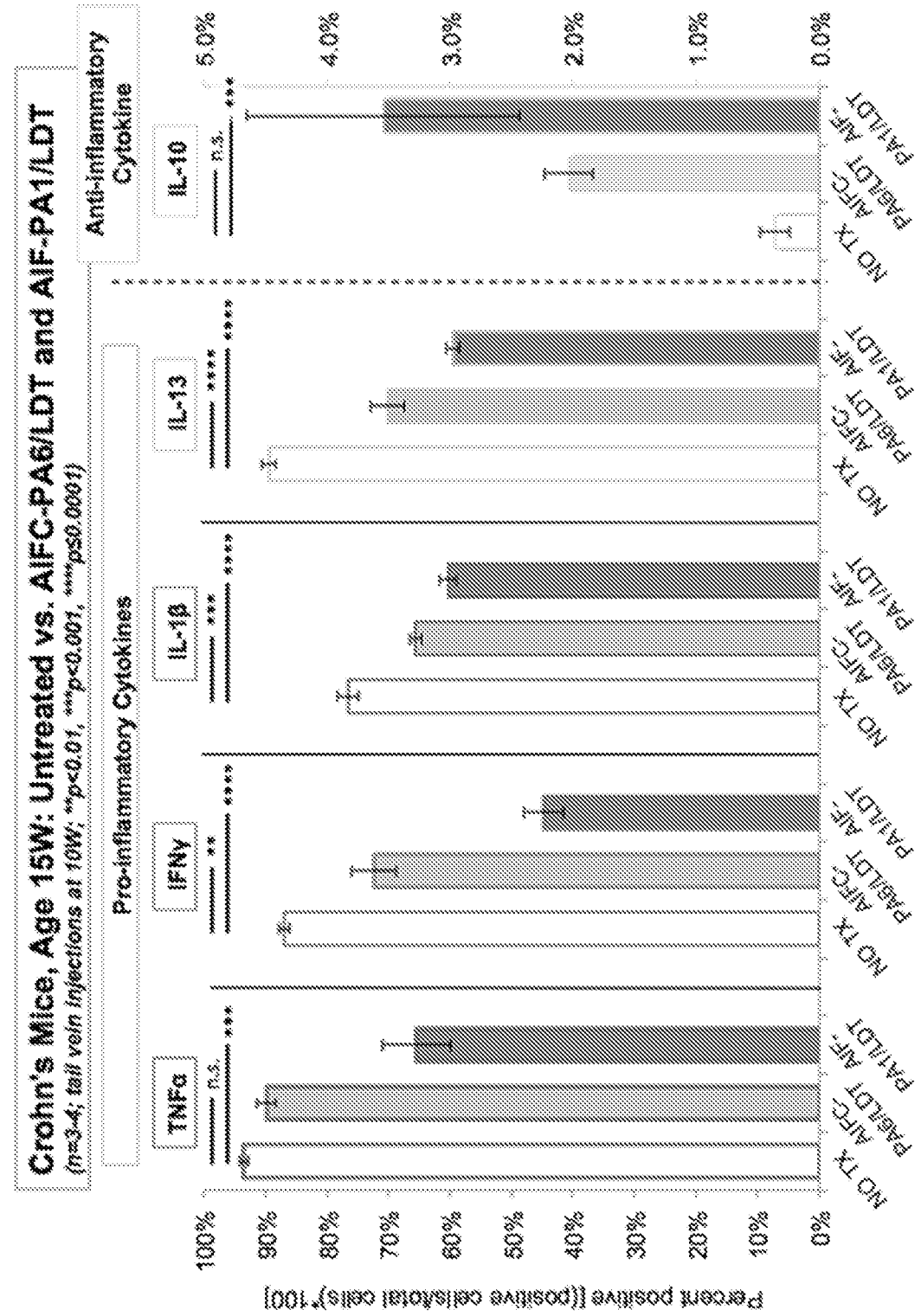
FIG. 6. Cytokine expression following treatment of SAMP1/YitFcsJ mice (Crohn's disease mice). Following the independent systemic injection of either AIFC-PA6/LDT or AIF-PA1/LDT into mice, animals were evaluated for the expression of specific inflammatory cytokines including tumor necrosis factor-alpha (TNFα), interferon gamma (IFNγ), interleukin-1 beta (IL-1β), and interleukin-13 (IL-13). These cytokines are pro-inflammatory in nature and are involved with the deterioration of intestinal tissue upon protracted exposure. Data demonstrate a statistically significant decrease in pro-inflammatory cytokines, TNFα, IFNγ, IL-1β, and IL-13 in AIF-PA1 treated animals compared to AIFC-PA6/LDT and untreated control animals. There was also a statistically significant increase in the anti-inflammatory cytokine interleukin-10 (IL-10) in the aforementioned groups compared to the control groups.

The SAMP1/YitFcsJ mouse closely mimics human Crohn's disease (CD) by exhibiting spontaneous formation of inflammatory-based intestinal lesions and other symptoms of intestinal ileitis. This pre-clinical model demonstrates close to 100% penetrance at an early stage in the mouse lifecycle and is amenable to data extrapolation to the human condition. In order to treat inflammatory lesions that have formed in the intestinal tracts, the following was performed:

Mice (10 weeks of age, female; n=4-7 per group) were brought to the animal holding/surgical room where they were weighed. Animals were placed in a restrainer and independently injected with the aforementioned anti-inflammatory peptide amphiphiles, [AIF-PA1/LDT (treatment; 1 mM) or AIFC-PA6/LDT (control; 1 mM] or untreated/no treatment control group. Approximately 100 μl of solution was injected into the tail vein of the mice. Animals were sacrificed at the 15 weeks of age. Animals were euthanized 5 weeks post-surgery and intestinal tissue was explanted, sectioned and stained with relevant inflammation based antibodies and data was quantified. Gross tissue samples were examined for pathology. Quantified data and results are summarized in FIGS. 4-6.

| SEQUENCES |
|---|
| MQMKKVLDS (SEQ ID NO: 1) |
| HDMNKVLDL (SEQ ID NO: 2) |
| KVLDPVKG (SEQ ID NO: 3) |
| KVLDGQDP (SEQ ID NO: 4) |
| DPVKG (SEQ ID NO: 5) |
| VVVAAA (SEQ ID NO: 6) |
| VVAA (SEQ ID NO: 7) |
| KVLD (SEQ ID NO: 8) |
| VVVAAAEEE (SEQ ID NO: 9) |
| VVVAAAEEEMQMKKVLDS (SEQ ID NO: 10) |
| VVVAAAEEEKLMSQKMVD (SEQ ID NO: 11) |
| KLMSQKMVD (SEQ ID NO: 12) |
| EEEAAAVVV-K (SEQ ID NO: 13) |

The invention claimed is:

1. A composition comprising branched peptide amphiphiles comprising:
   (a) a single nanofiber-forming moiety comprising: (i) a hydrophobic segment, a structural segment, and a charged segment, wherein the nanofiber-forming moiety self-assembles under aqueous conditions with other similar nanofiber-forming moieties to form a peptide amphiphile nanofiber;
   (b) an anti-inflammatory (AIF) peptide;
   (c) an additional functional moiety selected from a targeting moiety and a visualization moiety; and
   (d) a branchpoint, wherein the branchpoint is linked to the single nanofiber-forming moiety, the AIF peptide, and the additional functional moiety.

2. The composition of claim 1, wherein the additional functional moiety is a targeting moiety and comprises LDT.

3. The composition of claim 1, wherein additional functional moiety is a visualization moiety and comprises a small molecule fluorophore.

4. The composition of claim 1, wherein one or more additional functional moieties comprises a targeting moiety and a visualization moiety.

5. The composition of claim 1, wherein the peptide amphiphile is branched at one or more lysine residues.

6. A method of treating an inflammatory condition comprising administering a composition of claim 1 to a subject.

7. The method of claim 6, wherein the composition is administered systemically to the subject or locally to a site of inflammation.

8. The method of claim 6, wherein the inflammatory condition comprises a bowel disease.

9. The method of claim 8, wherein the composition is formulated as a suppository and is administered rectally.

10. The method of claim 8, wherein the composition is formulated for topical administration or injection and is administered by endoscope.

11. A system comprising:
    (a) the composition of claim 1; and
    (b) a medical device for administering the composition to a site of inflammation within the bowels of a subject.

12. The composition of claim 1, wherein the hydrophobic segment is a carbon chain of 8-20 carbons in length.

13. The composition of claim 1, wherein the structural segment comprises VVVAAA (SEQ ID NO: 6) or VVAA (SEQ ID NO: 7).

14. The composition of claim 1, wherein the charged segment is an acidic segment comprising a plurality of E and/or D residues.

15. The composition of claim 1, wherein the charged segment is a basic segment comprising a plurality of H, K and/or R residues.

16. The composition of claim 1, wherein the nanofiber-forming moiety comprises $C_{16}$-VVVAAAEEE (SEQ ID NO: 9).

17. The composition of claim 1, wherein the AIF peptide comprises MQMKKVLDS (SEQ ID NO: 1), HDMNKVLDL (SEQ ID NO: 2), KVLDPVKG (SEQ ID NO: 3), KVLDGQDP (SEQ ID NO: 4), DPVKG (SEQ ID NO: 5), peptides comprising only conservative or semi-conservative substitutions with respect to one or SEQ ID NOs 1-5, or peptides comprising at least 70% sequence identity with one of SEQ ID NOs 1-5.

18. The composition of claim 1, wherein the AIF peptide comprises KVLDS (SEQ ID NO: 8).

19. The composition of claim 1, wherein the nanofiber-forming moiety comprises $C_{16}$-VVVAAAEEE (SEQ ID NO: 9) and the AIF peptide comprises KVLDS (SEQ ID NO: 8).

* * * * *

SEQUENCE LISTING

```
<160> NUMBER OF SEQ ID NOS: 13

<210> SEQ ID NO 1
<211> LENGTH: 9
<212> TYPE: PRT
<213> ORGANISM: Artificial sequence
<220> FEATURE:
<223> OTHER INFORMATION: Synthetic peptide

<400> SEQUENCE: 1

Met Gln Met Lys Lys Val Leu Asp Ser
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic peptide

<400> SEQUENCE: 2

His Asp Met Asn Lys Val Leu Asp Leu
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3

Lys Val Leu Asp Pro Val Lys Gly
1               5

<210> SEQ ID NO 4
<211> LENGTH: 8
<212> TYPE: PRT
<213> ORGANISM: Artificial sequence
<220> FEATURE:
```

```
<223> OTHER INFORMATION: Synthetic peptide

<400> SEQUENCE: 4

Lys Val Leu Asp Gly Gln Asp Pro
1               5

<210> SEQ ID NO 5
<211> LENGTH: 5
<212> TYPE: PRT
<213> ORGANISM: Artificial sequence
<220> FEATURE:
<223> OTHER INFORMATION: Synthetic peptide

<400> SEQUENCE: 5

Asp Pro Val Lys Gly
1               5

<210> SEQ ID NO 6
<211> LENGTH: 6
<212> TYPE: PRT
<213> ORGANISM: Artificial sequence
<220> FEATURE:
<223> OTHER INFORMATION: Synthetic peptide

<400> SEQUENCE: 6

Val Val Val Ala Ala Ala
1               5

<210> SEQ ID NO 7
<211> LENGTH: 4
<212> TYPE: PRT
<213> ORGANISM: Artificial sequence
<220> FEATURE:
<223> OTHER INFORMATION: Synthetic peptide

<400> SEQUENCE: 7

Val Val Ala Ala
1

<210> SEQ ID NO 8
<211> LENGTH: 4
<212> TYPE: PRT
<213> ORGANISM: Artificial sequence
<220> FEATURE:
<223> OTHER INFORMATION: Synthetic peptide

<400> SEQUENCE: 8

Lys Val Leu Asp
1

<210> SEQ ID NO 9
<211> LENGTH: 9
<212> TYPE: PRT
<213> ORGANISM: Artificial sequence
<220> FEATURE:
<223> OTHER INFORMATION: Synthetic peptide

<400> SEQUENCE: 9

Val Val Val Ala Ala Ala Glu Glu Glu
1               5

<210> SEQ ID NO 10
<211> LENGTH: 18
<212> TYPE: PRT
<213> ORGANISM: Artificial sequence
<220> FEATURE:
<223> OTHER INFORMATION: Synthetic peptide
```

```
<400> SEQUENCE: 10

Val Val Val Ala Ala Ala Glu Glu Glu Met Gln Met Lys Lys Val Leu
1               5                   10                  15

Asp Ser

<210> SEQ ID NO 11
<211> LENGTH: 18
<212> TYPE: PRT
<213> ORGANISM: Artificial sequence
<220> FEATURE:
<223> OTHER INFORMATION: Synthetic peptide

<400> SEQUENCE: 11

Val Val Val Ala Ala Ala Glu Glu Glu Lys Leu Met Ser Gln Lys Met
1               5                   10                  15

Val Asp

<210> SEQ ID NO 12
<211> LENGTH: 9
<212> TYPE: PRT
<213> ORGANISM: Artificial sequence
<220> FEATURE:
<223> OTHER INFORMATION: Synthetic peptide

<400> SEQUENCE: 12

Lys Leu Met Ser Gln Lys Met Val Asp
1               5

<210> SEQ ID NO 13
<211> LENGTH: 10
<212> TYPE: PRT
<213> ORGANISM: Artificial sequence
<220> FEATURE:
<223> OTHER INFORMATION: Synthetic peptide

<400> SEQUENCE: 13

Glu Glu Glu Ala Ala Ala Val Val Val Lys
1               5                   10
```